United States Patent [19]

Cais

[11] 4,205,952
[45] Jun. 3, 1980

[54] SPECIFIC BINDING ASSAY METHOD AND REAGENT MEANS

[75] Inventor: Michael Cais, Haifa, Israel

[73] Assignee: Technion Research & Development Foundation Ltd., Haifa, Israel

[21] Appl. No.: 795,457

[22] Filed: May 10, 1977

[30] Foreign Application Priority Data

May 31, 1976 [IL] Israel ............................................. 49685

[51] Int. Cl.² ............................................. G01N 33/16
[52] U.S. Cl. ................................... 23/230 B; 23/910; 23/915; 252/408; 424/12
[58] Field of Search ......................... 23/230 B; 424/12; 252/408

[56] References Cited

U.S. PATENT DOCUMENTS

| | | | |
|---|---|---|---|
| 3,899,298 | 8/1975 | Szczesniak | 23/230 B |
| 3,966,556 | 6/1976 | Rubenstein | 424/12 X |
| 4,022,876 | 5/1977 | Anbar | 424/12 X |
| 4,036,823 | 7/1977 | Soares | 424/12 X |

OTHER PUBLICATIONS

Chemical Abstracts, 75: 61339n (1971).
Hackh's Chemical Dictionary, J. Grant, ed., 4th Edition, p. 264, McGraw-Hill, New York, 1969.

*Primary Examiner*—Sidney Marantz
*Attorney, Agent, or Firm*—Beveridge, DeGrandi, Kline & Lunsford

[57] ABSTRACT

A method and reagent means for the determination of small quantities of chemical compounds in man, animal and plants by a specific binding assay technique.

The method involves the utilization of a labelling constituent comprising a conjugate of a labelling substance and a binding component said labelling substance being one or more metal atoms which can be easily determined. The labelling constituents are selected from various metalo organic derivatives or metal coordination complexes.

The method is very specific and sensitive and can be successfully utilized for the determination of haptens selected from various groups such as alkaloids, barbiturates, steroids, cannabinoids, vitamins, aminoacids, tranquilizers, sugars, penicillins, etc.

35 Claims, No Drawings

SPECIFIC BINDING ASSAY METHOD AND REAGENT MEANS

The present invention relates to a new method and reagent means for the determination of the presence of small quantities of chemical compounds. More specifically the invention relates to an accurate, efficient and specific analysis of small quantities of chemical compounds in man, animals and plants by a specific binding assay technique.

Today there is a continuous demand for rapid and accurate quantitative determinations of chemical substances present in very low concentrations in body fluids such as blood, saliva or urine. These chemical substances can derive either from naturally occurring physiologically active compounds or from ingested drugs and/or their metabolites. These drugs belong either to the class of compounds administered medically for therapeutic purposes or they can be drugs of abuse such as narcotics and other poisoning materials. Of most importance is the determination for diagnostic purposes of particular compounds which may be indicative of the proper function, or otherwise, of body processes. Also for instance in case of poisoning, an easy and rapid method for determining the toxin could be extremely important in order to provide the required antidote. Obviously, one of the demands of these determinations is the specificity of the assay to be free of interferences by other components of the sample taken for analysis. Actually this is the main disadvantage of a large number of known techniques such as ultraviolet and visible spectrophotometers, fluorometers, mass spectrophotometer, chromatographic methods, wherein various degrees of non-specificity and interferences cause that these techniques could not be practically applicable. A recent special issue of the Journal of Chromatographic Science, 1974, (volume 12, p. 209–336) devoted to the "Analysis of Drugs of Abuse" reviews in a very concise manner the state of the art of the various methods.

The development of analytical methods incorporating specific binding assay techniques ino the area of assaying liquids, such as biofluids, for ligands, such as drugs of abuse, has resulted in highly increased levels of sensitivity of detection. Among the known methods, the following four specific binding assay techniques can be mentioned: Radio immunoassay (R I A), free radical assay technique (FRAT), hemaglutination inhibition (HI) and enzyme multiplied immunoassay technique (EMIT). Specific binding assays are based on the principles of monitoring specific binding reactions in which the extent of binding is a function of the amount of unknown ligand present by means of a labelled component.

Following are examples of how the prior art methods treat the detection of a drug, one type of material determinable by specific binding technique.

In the radio immunoassay, the drug is labelled with a radioactive isotope such as for example $^{125}I$, or $^{14}C$. After allowing a mixture of unlabelled drug, labelled drug and antibody to reach an equilibrium, the antibody-bound drug is separated by one of the usual separation techniques e.g. by precipitation with ammonium sulphate. The amount of free and/or bound labelled drug is determined by measuring the radioactivity of the supernatant liquid or of the precipitate. Although this method is very sensitive and specific, it has as a main drawback, the utilization of radioactive materials which impose technical skills for handling, disposal problems and also requires expensive apparatus. These special requirements do not allow for the wide and general use of these determinations, in particular for small laboratories.

In the free radical assay technique, a spin-labelled hapten is synthesized by attaching a relatively small nitroxide molecule to the drug. Haptens, as known are defined as substances which by themselves on injection, because of their small size, do not give rise to antibodies but if bound to larger carrier molecules can induce the formation of antibodies specific for the free hapten. The free tumbling species gives a high sharp electron spin resonance spectra. When the spin-labelled hapten is complexed with the antibody, the rate of tumbling decreases, causing a broadening of the Electron Spin Resonance pattern. In the presence of drug, the spin-labelled hapten is displaced and an increase in the Electron Spin Resonance (ESR) signal is noted. The amount of the unbounded drug is proportional to the magnitude of the Electron Spin Resonance peak intensity. Unknown concentration may be determined by comparing the ESR peak heights with those of standards. The drawbacks of this method are the expensive equipment required and the relative low sensitivity. In the hemagglutination inhibition, red blood cells are coated with the drug-carrier protein complex. In the absence of the drug, the antibodies will agglutinate the treated red blood cells. Free drug, if present, will bind to the antibody. Since the antibody has been consumed, hemagglutination is inhibited and the red cells form a pellet in the top of the conical-shaped wells. The sensitivity of the hemagglutination inhibition may be adjusted over a wide range since inhibition of agglutination is dependent upon the amount of antibody present. Although this method is considered to give reliable results, it has the disadvantage that the completion of analysis requires relatively a long time and the interpretation of the results is largely subjective.

In the Enzyme Multiplied Immunoassay techniques, the drug is labelled with an active enzyme (e.g. lysozyme) which is capable of breaking down the cell wall of bacteria. Drug molecules attached to the surface of lysozyme do not interfere with enzymatic activity. When the antibodies are bound to these labelled drug, the substrate is sterically hindered from approaching the active enzyme sites; unlabelled drug displace enzyme - labelled drug which in turn results in an increased enzyme activity. By measuring the optical densities at the start and the completion of the analysis, one can approximate the quantity of unlabelled drug in the unknown sample. By lengthening the time of enzymatic action, the sensitivity of the assay may be increased. The disadvantage of this method lies in the relatively poor sensitivity, the rather high costs of the reagents, and the intrinsic instability of enzymatic reagents.

Although each of the above-mentioned specific binding method may be breakthroughs in their own right in determination of small amounts of drugs, from the above review of the known methods, it appears that there is still a long felt need for a more convenient method of this type.

It is the object of the present invention to provide a convenient specific binding assay method for the determination of small amounts of unknown compounds. It is another object of the present invention to provide a convenient specific binding assay and reagent means for the determination of small amounts of unknown compounds, which method is very sensitive, and very specific without employing radioactive reagents. Thus the invention consists of a heterogenous specific binding assay method for assaying a liquid medium for a ligand, which method comprises:

(a) contacting said liquid medium with reagent means which includes a labelled constituent comprising a conjugate of a labelling substance and a binding component and which forms, with said ligand to be determined, a binding reaction system producing a bound-phase and a free-phase of said labelled constituent, the quantity of labelling substance resulting in said bound-phase being a function of the amount of said ligand present in said liquid medium;

(b) separating said bound-phase from said free-phase; and (c) determining the quantity of labelling substance in either the bound-phase or the free-phase, characterized in that said labelling substance is a metal atom or atoms and the quantity thereon in either the separated bound-phase or free-phase is determined.

As discussed more fully below, the binding reaction system may take the form of any of the known conventional heterogenous techniques such as those presently employed in radio-immunoassays and heterogenous enzyme immunoassays.

The specific binding reagent means may take many different forms. In general, such means comprises three basic constituents, which are: (1) the ligand to be detected, (2) a specific binding partner of the ligand, and (3) a labelled constituent which is normally a labelled form of (a) the ligand, (b) a specific binding analog of the ligand, or (c) the specific binding partner. The binding reaction constituents are combined simultaneously or in a series of additions, and with an appropriate incubation period of periods the labelled constituent becomes bound to its corresponding competing binding partners such that the extent of binding, i.e the ratio of the amount of labelled constituent bound to a binding partner to that unbound, is a function of the amount of ligand present. To follow is a brief description of some of the different binding reaction schemes that may be used in carrying out the method of the present invention with heterogenous binding formats.

For the diagrams which are set out hereinafter, the following legend shall apply:

| Symbol | Definition |
|--------|------------|
| L | ligand to be detected |
| ⓛ | ligand or specific binding analog thereof |
| B | binding partner for the ligand |
| * | labelling substance, i.e. metal atom |
| ins. | insoluble phase |
| → | incubation period followed by an appropriate separation |
| (lim) | limited; present in an amount less than that capable of being bound to the total available binding sites under the selected reaction conditions during the selected incubation period; i.e. the constituent for which the other constituents compete for binding. |
| (exc) | excess, present in an amount greater than that capable of being bound by the total available binding sites under the selected reaction conditions during the selected incubation period. |

HETEROGENEOUS BINDING FORMATS

1. Competitive binding formats
   (a) L+ ⓛ * +B(lim)→+insolubilizing agent for B or ⓛ * References: Biochem. J. 88:137(1963) and U.S. Pat. No. 3,839,153.
   (b) L+ ⓛ *+ins.B(lim)→ References: U.S. Pat. Nos. 3,505.019; 3,555.143; 3,646.346; and 3,654.090.
   (c) L+B* + ins. ⓛ (lim) → Reference: U.S. Pat. No. 3,654.090.
   (d) L+ins. ⓛ +B*(lim) → Reference: U.S. Pat. No. 3,850.752.

2. Sequential saturation formats
   (a) L+B (exc)→+ ⓛ * (exc)+insolubilizing agent for B or ⓛ *
   (b) L+ins. B (exc)→+ ⓛ * (exc) Reference: J. Immunol. 209:129(1972) and U.S. Pat. No. 3,720.760.
   (c) L+B* (exc)→+ins. ⓛ (exc)→Reference: Nature 219:186(1968).

3. "Sandwich" format
   L+ins. B (exc)→+B* (exc)→Reference: U.S. Pat. No. 3,720.760.

4. Solid-phase dilution format
   L+ ⓛ * +ins. (nonspecific)→+B (lim)→ Reference: U.S. Pat. No. 3,659.104.

For further discussion of the parameters involved in conventional heterogeneous assay systems, such as more detailed descriptions of assay formats and alternative separation techniques, reference may be had to Principles of Competitive Protein-Binding Assays, Ed. Odell and Daughaday (J.B. Lippincott Co., Philadelphia 1972).

It is contemplated that manipulative schemes involving other orders of addition and other binding reaction formats may be devised for carrying out heterogeneous specific binding assays without departing from the inventive concept embodied herein.

For the purpose of providing a detailed description of a preferred form of the present method and reagent means, a system will now be described wherein a hapten is determined by providing a binding for such hapten and a metal atom-labelled form of the hapten ("metallo-hapten") such that binding sites on said binder are occupied by said metallo-hapten, allowing the specific binding reaction to occur by introduction a sample suspected of containing said hapten, separating the non-bound metallo-hapten, and determining the concentration of the metal atom therein by a convenient method such as for example by atomic spectrometry. The paragraphs which follow refer to this method, as illustrating examples.

The binding sites can be occupied either in the range between 95% and 100% in which case we are displacing only a small amount of the occupied sites at the equilibrium state, or they can be partially occupied in which case the labelled and the unlabelled hapten will have to compete for both the binding sites which were previously occupied by the labelled hapten as well as compete for the large number of binding sites which may be free. In this case the displacement will be done at the lower concentration of the mixture and this may require special separation methods.

In a medium containing only metallo-hapten and binder, at equilibrium, binder sites will be occupied by the metallo-hapten. Upon adding to the medium a small amount of hapten, the hapten and metallo-hapten will compete for available binder sites. By performing a metal content determination in the separated solution, prior to the hapten addition and after the hapten addition, the relative concentrations of the metal content at equilibrium will be measured. By employing known amounts of the hapten, the effect on the equilibrium can be easily determined from metal content measurements of the binder-metallo-hapten system, or the free metallo-hapten, or both components. Thus the method requires first to determine the metal content in calibrated standards solutions containing metallo-hapten and then to test the separated solution containing the hapten. Once the metal in the standards has been determined the method can be automated to enable specific and accurate analysis of a large number of samples. The method according to the present invention is carried out normally at ambient temperature which is also the preferred one. For certain systems incubation at 36° C. will be required so that generally the temperature range will be between 0° to 50° C. A person skilled in the art will certainly know how to select the proper temperature in accordance with the specific system on which the assay is carried out, considering the factors involved such as stability of the metallo-hapten, requirement of incubation etc.

The separation of the liquid phase from the solid can be performed by any technique known in the art such as filtration, centrifugation etc. This operation is also encountered in the radioimmunoassay and the various means utilized therein, may also be successfully applied in the method according to the present invention.

The method is very convenient to be carried out and overcomes the several drawbacks of the radioimmunoassay technique. At the same time the method can be very specific and sensitive and can attain substantially the same accuracy as radioimmunoassay.

One of the advantages of the method according to the present invention is the easy analysis of a compound through the determination of the metal component. Various easy methods are now known for a metal determination such as emission, absorption and fluorescence spectrometry, various electrochemical methods and neutron activation. In particular common use is the atomic absorption determination of metals which is now recognized as a very sensitive and accurate method, a fact which attests to the versatility of the present invention even for the determination of very small amounts of unknown compounds in a broad range of applications. The sensitivity of atomic absorption spectrometry has been discussed in a recent review (Atomic Absorption Newsletter 11,37, 1972). The introduction of flameless methods (e.g. graphite chamber through which electric currents pass, dry and atomize the sample at temperatures up to 3,700° C.) has increased the sensitivity by orders of magnitude. Therefore most reliable results can be obtained even with very small aliquots of the tested substance. For example, in determination of Co, the detection limit with the common atomic absorption instrument (Model 403) is 0.01 μg/ml, while with a graphite chamber (HGA - 2000 instrument) the detection limit is 0.00004 μg/ml. In the following table the atomic absorption detection limits of some elements determined by graphite chamber (HGA - 2000) are given.

TABLE 1.

| The Element | Detection limit μg/ml | The Element | Detection limit μg/ml |
| --- | --- | --- | --- |
| Manganese | 0.00001 | Bismut | 0.0001 |
| Silver | 0.0000025 | Cadmium | 0.000001 |
| Silicon | 0.00008 | Cobalt | 0.00004 |
| Aluminium | 0.00003 | Iron | 0.00003 |
| Zinc | 0.0000006 | Nickel | 0.0001 |
| Gold | 0.00008 | Antimony | 0.0002 |
| Lead | 0.00006 | Thallium | 0.00014 |

This Table is only partial for some of the elements, and is hereby given only in order to illustrate the very low detection limit which can be attained by this type of atomic absorption instrument. Thus the high sensitivity of detection by atomic absorption spectrophotometer can bring this method within the sensitivity limits of radioimmunoassay technique, without incurring the disadvantages connected with the use of radioactive labelled components. Although in the context of the present specification, the determination of the metal is mentioned to be performed by atomic absorption or emission measurement, it should be clearly understood that any other known methods for the metal determination, can be successfully used. Thus for example a recent report on the use of microwave excitation emission spectrometry (Kawaguchi and Valee, Anal. Chemistry, 47, 1029–1034, 1975) mentions determination of metals in metallo-enzyme in the range of $10^{-11}$ to $10^{-13}$ gram of metal on an absolute basis. It may also be assumed that advances in anodic stripping voltametry would also provide another simple and inexpensive technique for concentration measurements of the metals in the systems present in the method according to the present invention. The determination of the metal content by atomic absorption or emission spectrophotometer is now a common expedient which can be performed easily even in a small laboratory. One could also envisage the possibility of using an electrochemical deposition method on a metal wire such as for example a tantalum wire and determining the amount of material by introduction of the sample into the atomic spectrophotometer.

The recent developments of multichannel atomic absorption spectrometers [Analytica Chim. Acta, 87,301(1976)] capable of analysing up to nine elements simultaneously further expands the potential applications of metallo-haptens in the development of multitest systems.

Although all immunochemically active substances can be determined by the method according to the present invention, they are particularly suitable for assaying substances in very small quantities, for, a very high sensitivity can be reached.

The performance of an assay requires the hapten, the metallo-hapten and the binder besides an instrument for the metal determination such as atomic absorption spectrophotometer. The metallo-hapten and the binder are available either in a solid form or in solution. When they are in a solid state, any suitable solvent or solvent mixture can be used. In particular preferable for the analysis of biological fluids, are aqueous solutions. In these cases it will be desirable to have the assay mixtures buffered, so as to maintain a pH in the range of 5 to 10.5 and preferably 6.5 to 8.5. Any suitable buffer can be successfully used provided that it will be free of certain impurities of the same metal as incorporated in the metallo-hapten which will affect the sensitivity, or does not contain substances which might cause undesirable interferences during the atomic absorption spectrophotometric determinations. Examples of some preferred buffers are:

Alkali metal and ammonium phosphate e.g. sodium and disodium phosphate, alkali metal and ammonium citrate or maleate, ethylene diamine tetra-acetic acid etc. The substances, haptens which can be determined are limited primarily by their ability to be attached to the binder sites. No particular limitations can be imposed to the specific molecule of hapten to be determined. Generally the molecular weight will be between 100 and about 100,000. But this does not preclude the use of macro-molecules of a much higher molecular weight. Commonly the molecular weights of these haptens will be in the range of 125 to 5,000.

From the known nomenclature of these haptens the following groups can be envisaged for their analysis:

Alkaloids, such as: morphine, codeine, dihydrocodeine, heroin, oxymorphone, metopon, pholcodine, etc.
Barbiturates, such as: Veronal, luminal, seconal, phenobarbital, barbital, etc.
Steroids, estrogens such as: $\beta$-estradiol, estrone, estriol, 17$\alpha$-ethyinyl estradiol etc., androgens, progestogens; adrenocortical hormones, etc.
Cannabinoids and their metabolites.
Vitamins, such as: Carothene, riboflavine, thiamine, niacin, ascorbic acid, tocopherol, phytyl-1,4-naphtoquinone, etc.
Amino acids and polypeptides
Sugars, including saccharides and polysaccharides.
Tranquilizers, such as: meprobamate, valium, oxazepam, phenotiazines, etc.

In addition to the above haptens other miscellaneous compounds such as cocaine, prostaglandin, antibiotics such as penicillin, chloromycetin, actinomycetin and nucleic acids and nucleotides; insecticides, fungicides, bacteriocides and nematocides such as malathion, carbamates, etc. can also be assayed with the method according to the present invention. In general, antigens, haptens and their antibodies, hormones, vitamins, drugs, metabolites and their receptors and binding materials may be determined using the present method.

The binder is generally a high molecular weight material which has sites which recognize specific structures. The macromolecules of greatest interest are proteins and nucleic acid which are found in cell membranes, blood and other biological fluids. These compounds include enzymes, antibodies, ribonucleic acid and deoxyribonucleic acid. The most convenient group of protein for use in the present invention are antibodies. Antibodies are produced by introducing an immunogenic substance into the blood stream of a living animal. The result of the introduction of the immunogenic substance for antigen is the production of antibodies which act to coat the antigen and detoxify it or precipitate it from solution. The protein forms a coat which is geometrically arranged so as to have the antigen fit the spatial arrangement of the protein. The material to be assayed is bonded to a protein by any convenient means and the modified protein introduced into the blood stream. The antibodies which form will include groups of antibodies which are shaped to fit the hapten bonded to the protein.

Preferably as binders are the protein-based compounds which are readily available. Particularly useful are the insoluble binders which will facilitate the entire method according to the present invention. In this case the amount of hapten present in the system, determines the amount of metallo-hapten bound to the sites of the binder. Soluble binders (antibodies) are rendered insoluble by their linking to an insoluble support such as cellulose glass beads, synthetic polymers etc.

The present method also encompasses the case when the hapten is insolubilized and a certain solubility of the binder is involved, giving rise to a metallo-binder derivative. In this case the distribution of the metallo-binder between the insolubilized hapten and the solution, enables the measuring of the unlabelled binder.

Another variation also included in the present invention is the case wherein some hapten is soluble along the binder as in the previous case and thus the system comprises hapten, metallo-binder and some insolubilized hapten. The distribution of the metallo-binder between the liquid and solid phase enables the accurate determination of the hapten in solution. Of course other embodiments which are in the scope of the present invention can be easily envisaged by a person skilled in the art, and the above-mentioned variations are not the only ones covered by the invention. For instance it is also possible that the antibodies may be bonded to various supports such as polyacrylamides, copolymers of vinyl acetate and acrylic acid, polyvinyl esters, modified cellulose etc. The advantage of the support is that the antibody may be easily separated from the solution in this manner and thus the clear solution easily analyzed. A description and various examples of the coupling of metallo-haptens to protein are described in, for example in the reference Methods of Immunology and Immunochemistry, Vol. 1 (Chase and Williams, Academic Press, 1967). The methods are described thereby for the preparation of conjugates for immunisation, but they can also be used for the preparation of the coupling of the metallo-haptens to proteins.

A basic requirement of the method of this invention refers to the metallo-haptens. Due to the important role of this component for the method according to the present invention, some more explanation on metallo-hapten structure and metal organo derivatives and principles of their general methods of preparation is hereinafter presented. In order to give a better definition of the metallo-hapten, we shall refer to two general classes of compounds which could incorporate metal atoms in their structure. We can envisage organometallic compounds in which there is a direct bond between carbon atoms of the organic moiety and the metal atoms, or consider the general class of coordination complexes of a metal. The latter can include (in addition to the previously mentioned organometallic compounds) also the very large variety of compounds in which there is a chemical bond between the metal atom and another atom, not necessarily a carbon atom, which is present in the organic moiety.

The organic moiety can be practically any organic compound provided that it contains a suitable functional group with which one can form a bond to the metal atom. In order to further illustrate the versatility and potential of this method, it would seem adequate to define here two general approaches in the preparation of metallo-haptens. One approach is by introducing a metal atom or atoms directly into the hapten which is under investigation. This will be a metallo-hapten which subsequently will be used in the assay as will be described later.

The second approach could be in the preparation of a metal-containing reagent which will also incorporate a suitable functional group by means of which one can attach the metal reagent to the hapten desired to be assayed. In other words we can have specific haptens with specific metal atoms introduced by usual and available procedures, or we can prepare a general reagent or reagents again with a wide variety of metal atoms and these could then be attached to the hapten in question. As an example, if the hapten contains a carboxylic group in its structure we can prepare a metal reagent in which one of the ligands attached to the metal has an additional amino functional group or hydroxyl alcoholic functional group which can then be reacted with a carboxylic group of the hapten forming an amide linking or an ester link and in this way the metal containing reagent would become the label for that hapten. It thus becomes very easily apparent that any reactive functional group could be used either in the hapten or the metal containing reagent and the specific selection will entirely depend on the structures and chemical properties of the haptens involved. Further specific examples to illustrate this selection will be given in the context of the specification.

In order to further illustrate the high versatility of the new invention, we shall now try to give a few indications of how a metallo-hapten can be prepared by using the various classes of compounds and various methods for introducing metals into the desired haptens. We shall first refer to organometallic compounds according to the definition that was previously mentioned, namely compounds in which there is a direct carbon to metal bond. It is generally recognized that one can divide these organometallic compounds into three major categories according to the type of chemical bond that is formed between the carbon atom and the metal atom.

(1) There are the so-called ionic bounds as for example the compounds such as butyl sodium or a Grignard reagent, where the carbon-metal bond is very largely ionic.

(2) There are sigma covalent bonded derivatives such as for example derivatives of mercury like diaryl mercury or dialkyl mercury or alkyl mercury chloride or tetra-ethyl lead in which the carbon to metal bond is primarily covalent.

(3) The third class of compounds are compounds in which there is a so-called pi-bond in which a metal atom of the transition series such as for example iron or cobalt or nickel can react or interact with pi-electrons of an unsaturated organic compound. In addition to the donation of the pi-electrons of the organic moiety into empty orbitals of the metal atom there is a so-called back-donation in which electrons found in occupied orbital of the metal atoms, interact with empty orbitals of the organic moiety, thereby forming an additional bond which is of the pi-symmetry type as recognized in chemistry. This class of compounds are susceptible to a wide range of reactions.

Of these three classes the more interesting will be those in which we have a direct covalent bond or a pi-bond. The ionic metal-carbon bonds are less interesting because in a dissociating medium the ionic metal-carbon compound can dissociate and we may not be able to keep the metal atom to which the ligand is attached in the position desired. A covalent bond such as for instance mercury-carbon bond may be considered as an useful illustration. Let us take as an example a steroid such as estradiol or estriol in which there is an aromatic ring. This can be easily mercurated by a reaction between the steroid and mercuric acetate in order to substitute one (or more) of the hydrogen atoms in the aryl ring by a group (or groups) containing mercury atoms and thereby arrive at a compound which incorporates the mercury atom through a stable carbon-mercury bond and this can afterwards be used as the metallo-hapten for the specific binding assay.

We can illustrate another example by using the pi-type bonding whereby we have an organic moiety which includes a grouping such as an allyl chloride or allyl alcohol. By reacting such an allyl chloride with metal atoms such as palladium or nickel or platinum we may form a piallyl nickel or pi-allyl palladium, or pi-allyl platinum compounds whereby there is a relatively strong chemical bond between the metal atom and the allyl electronic system of the organic moiety. Such a compound could then again be used as the metallo-hapten for the specific binding assay. We could on the other hand react a suitably substituted organic moiety with compounds such as ferrocene in which the iron atom is strongly bonded to two cyclopentadienyl groups. We could react the organic moiety with any other such so-called "sandwich" compound or metallocene, in which atoms other than iron are used such as cobalt or nickel or manganese, with suitable ligands and by carrying out a typical organic reaction, as for example doing a Friedel-Crafts reaction, on the ferrocene and thereby to obtain the incorporation of the ferrocene; in other words introduction of an iron atom into the hapten which we are trying to assay.

Another possibility for instance is by taking a ferrocene or cobaltocene or similar structures in which there is a substituent group or functional group, which can react with an organic functional group of our hapten. For instance if we take an amino-ferrocene and react this with a carboxylic acid derivative of our hapten, we can form an amide group and thereby incorporating the ferrocene moiety and thus introducing the iron atom into the hapten which we are trying to assay.

By taking the previous example with the steroid estrogen for instance estradiol, one could react this material with chromium hexacarbonyl, in order to form an arenechromium tricarbonyl type of complex, which would have the incorporation of a chromium atom into the hapten to be assayed.

It is beyond the scope of the present specification to enter into further details on the principles of preparation of the metallo-haptens. The present literature is fortunately abundant with the vast number of metal organo-derivatives known in the art and provides the possibility of design and synthesis of any desirable compound. Any person skilled in the art, after reading the present specification with the principles illustrated for selecting the proper metallo-haptens, will certainly be in a position to apply the method of specific binding according to the present invention.

A general formula envisaged for the metal organo-derivatives used in the preparation of the metallo-haptens is $M_m L_n^1 L_o^2 L_p^3 L_q^4 L_r^5 L_s^6$, wherein L represents the ligands forming the chemical bond to the metal atom (M).

This bond can be either through carbon-metal interaction, or through an interaction of the metal atom with an atom (or atoms) other than carbon. In the first case the compound is generally referred to as organo-metallic compound while in the latter case the compound is designated as metal coordination complex. The ligand $L^1$ through $L^6$ may be all the same, different or mixtures of same and different. The subscripts n through s represent the number of atoms or ligands per molecular formula, wherein m can have any integer value from 1 to 10 and preferably between 1 and 4. It is of course also possible that the metal M can represent the chemical formula of two or more metal elements and this is the case when m is at least 2. The subscripts n through s can have any numerical value from 0 to 12 provided that the sum of these subscripts (n+o+p+q+r+s) should correspond to the coordination number of the metal atoms (M), when m=1. In the case that m is higher than 1, it is necessary to count the sum (n+o+p+q+r+s) for each metal atom M separately so that this sum corresponds in each case to the coordination number of the metal atom M under consideration.

The metal may be any metal element or combination of metal elements and preferably metal elements selected from the transition metals of group IB, IIB, IIIB, IVB, VB, VIB, VIIB and VIII of the Periodic Table of elements. Particularly useful are the so-called noble metals from group VIII such as Ru, Rh, Pd, Ir and Pt. For example the element Platinum occupies a special position in the organo-metal complex chemistry due to the variety of compounds which this element can form. Due to the fact that Pt can exist in many oxydation states from 0 to +4, the number of platinum organocompounds is very high so that any desired complex can be envisaged and reduced to practice. Other elements which have metal-like properties, such as As, B, Sb, Se, Si, Sn, Te, Ge, as well as the lanthanides elements could be used to prepare metallo-haptens.

Among the important organic moieties groups to be present in the coordination complexes, the following non-limiting examples are mentioned:

Pyridine, ethylene diamine, diethylenediamine, dimethyl glyoxime, dipyridyl, phenantroline, acetylacetonate, ethylene diamine tetraacetic acid etc.

These groups are linked by a functional group R, which is not involved in coordination to the metal but merely serves as handle for making a chemical bond with the hapten. The selection of the proper metallo-hapten to be used as a component in the system according to the present invention, depends on some properties such as the specific activity requested and the simplicity of the determiniation of the metal.

According to another embodiment for carrying out the method according to the present invention, use can be made of a test pack kit composed of:

(a) A given quantity of a metallo-hapten, selected according to the hapten to be determined.

(b₁) A given quantity of the binder to be used in the system, or (b₂) A known amount of an antibody in an insoluble form.

If required the test pack kit can also contain the buffer and the necessary auxiliaries for making a dilution series of the sample to be examined for a quantitative determination such as test tubes, pipettes and flasks with dilution liquids.

One of the most important aspects of the present invention is the practically unlimited versatility in tailor-making the metal-labelled haptens for application to the desired specific binding assay. Upon disclosure of the general principles and components of this invention, it will be possible for any person skilled in the art to devise innumerable variations of the reagent means and procedures described herein.

The invention is further illustrated by the following examples which are not to be construed as limiting the invention to the specific procedures described in them. It will be obvious that certain changes and modifications may be introduced within the scope of the invention.

The various abbreviations and symbols used in the examples are listed below:

AAS = Atomic absorption spectroscopy
OVA = Ovalbumin
BSA = Bovine serum albumin
DMF = Dimethylformamide
Fc = The ferrocenyl moiety C₅H₅FeC₅H₄—
DCC = Dicyclohexylcarbodiimide
PBS = Phosphate Buffer saline NHS = N-hydroxysuccinimide: 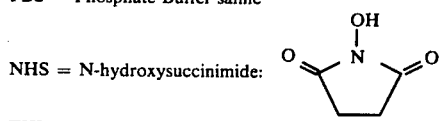

THF = Tetrahydrofuran
IR = Infra Red
NMR = Nuclear Magnetic Resonance
TLC = Thin layer chromatography
acac = Acetylacetonate ligand

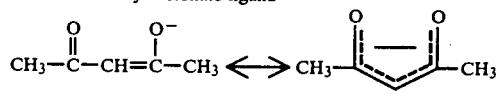

Cr(acac)₃ = tris-acetylacetonatechromium

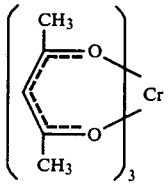

Cym = The cymantrenyl moiety [CO]₃MnC₅H₄—
(acac)₂ Cr(acac)-NH₂ = monoamino-tris-acetylacetonate chromium

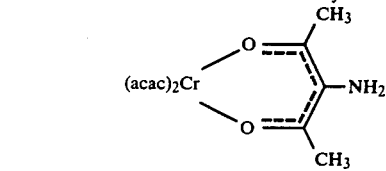

E₁ = Estrone

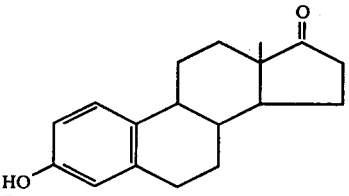

E₂ = Estradiol

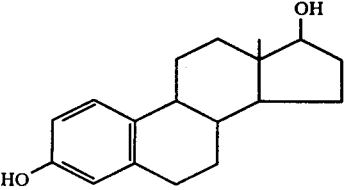

E₃ = Estriol

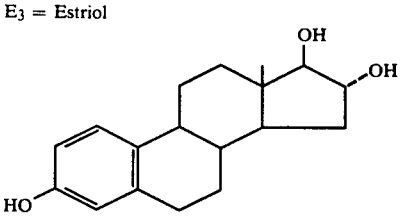

E₁(OX)—COOH = Extrone oxime-0-carboxymethyl

-continued

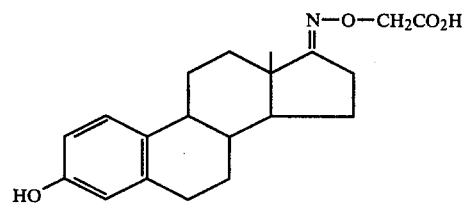
$E_2(HS)-COOH$ = Estradiol-17β-hemisuccinate

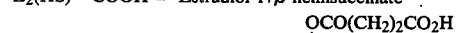
$E_3-(HS)_2$ = Estriol-16α, 17β-bis-hemisuccinate

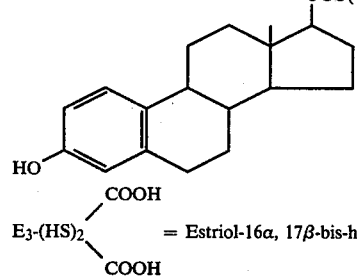
$E_1-NH_2$ = 1,3,5-Estratrien-3-ol-17-amino

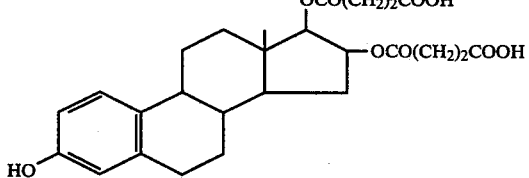
$(E_1)$-NOH = Estrone oxime

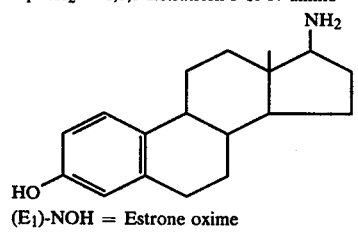
Pg—OH = 11α-hydroxyprogesterone

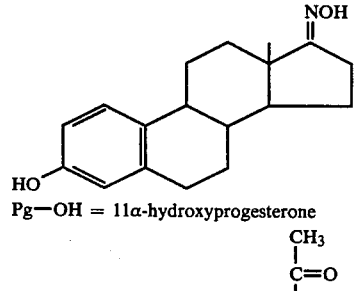
Pg(HS)—COOH = 11α-hydroxyprogesterone hemisuccinate

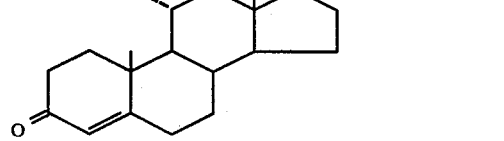

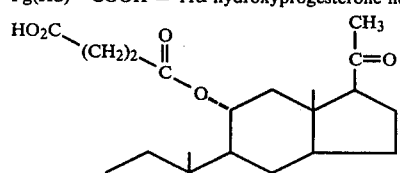
$\Delta^6$-THC = $\Delta^6$-Tetrahydrocannabinol

-continued

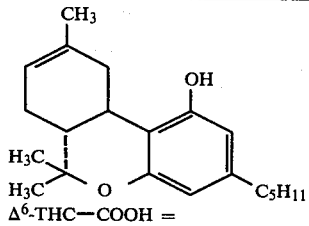
$\Delta^6$-THC—COOH = 7-nor-1-carboxy-$\Delta^6$-tetrahydrocannabinol

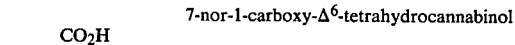

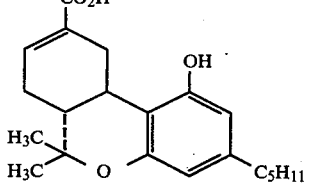

EXAMPLE I

Iron-labelled Bovine Serum Albumin (a) Triethylamine (0.14 ml, 1.0 m mole) and isobutylchloroformate (0.13 ml, 1.0 m mole) were added to a stirred, cooled solution (−15° C.) of ferrocenyl carboxylic acid, Fc - COOH (235 mg, (1.0 m mole) in dry DMF (3 ml). After stirring at −15° for 20 min. and further at room temperature for 1 hr., the reaction mixture was added dropwise to a stirred, cooled (0° C.) solution of BSA (400 mg. 0.006 m mole) in 60 ml water containing 2.6 g of sodium carbonate. Upon completion of the addition, stirring was continued at 4° C. for 22 hrs. The reaction mixture was centrifuged (16,000 rpm at 0° C.) for 30 min. and the supernatant liquid was dialyzed against borate buffer, pH 8.5 (3×2 l) and then against distilled water (4×2 l). Lyophilization of the dialysate yielded 380 mg of BSA - $(CO\ Fc)_n$ conjugate. The number of ferrocenyl moieties, Fc, per mole of BSA determined by classical U.V. differential analysis was found to be equal to approximately n=11.

In order to carry out the same determination by atomic absorption a calibration curve was first obtained by dissolving a known amount of Fc COOH in a solution of 0.1 NaOH (stock solution) followed by preparing suitable dilutions in the expected measurement range. A weighed amount of the BSA-$(COF_c)_n$ conjugate was then dissolved in a measured volume of 0.1 N NaOH solution and the solution was measured by atomic absorption using a Perkin Elmer Model 404 AS instrument at wavelength 250.6 nm, slit 3, flow 53/32.5, autozero on BSA. Interpolation of the ASS signals obtained in this measurement into the calibration curve provided the answer of n=16 ferrocenyl moieties per mole of BSA in the BSA-$(COFc)_n$ conjugate prepared above. This determination can be regarded as more accurate than the UV differential analysis method because in AAS the iron content in the molecule is measured directly.

(b) A solution of diferrocenylcarbonium fluoroborate, $(Fc)_2CH^+BF_4^-$ (15 mg, 0.03 m moles) in methanol (2 ml) was added to a cooled (0° C.) solution of BSA (80 mg, 0.0012 m mole) in 10 ml water containing 0.6 g of sodium bicarbonate. Even though the colour changed rapidly from dark-blue to yellow, the reaction mixture was further stirred at 0° for 15 hr. The solution was then centrifuged (16,000 r.p.m. at 0° C.) for 30 min and the supernatant was dialyzed against borate buffer, pH 8.5 (3×0.5 l) and then distilled water (5×0.5 l). Lyophilization of the dialyzate yielded 67 mg of BSA - $[CH(Fc)_2]_n$ conjugate. This conjugate showed a well defined band in electrophoresis different from that of the non-conjugated BSA starting material.

Atomic absorption measurement by the procedure described in (a) above showed n=11 in the BSA -$[CH(Fc)_2]_n$ conjugate, equivalent to 22 ferrocenyl moieties per mole of BSA.

EXAMPLE 2

The use of iron-labelled - BSA to determine Antibody concentration by Atomic Absorption Quantitative precipitation of the antibody - antigen combination, commonly called the Precipitin Reaction, is a widely used immunological technique for the determination of antibody concentration. The following description of a series of Precipitin Reactions demonstrate the use of metal-labelled antigens for the quantitative determination of antibody concentration.

Rabbit antiserum against bovine serum albumin (anti - BSA) (0.5 ml of a 1:16 diluted preparation) was mixed with antigen solution (0.5 ml of a range of solutions from 1 mg/ml to $4 \times 10^{-3}$ mg/ml) and incubated at room temperature for 2 hours. Each sample was then mixed on a Vortex Mixer and incubated for 24 hr. at 4° C. After centrifugation (4000 rpm for 30 min. at 0°) the supernatant liquids were decanted and the precipitates were washed twice with borate-saline buffer, pH 8.5. The precipitates were then dried and each one was dissolved in 1.0 ml of a solution of NaOH 0.1 N).

The above procedure was carried out with each one of the following antigens:

(i) BSA; (ii) BSA-$(CO Fc)_{16}$; (iii) BSA-$[CH(Fc)_2]_{11}$ Each one of the above solution was measured by two methods:

(a) By a Zeiss U.V. Spectrophotometer to determine the absorption at 287 nm and hence calculate the amount of protein precipitated through interpolation in a calibration curve prepared with BSA in 0.1 N NaOH solution.

(b) By using the AAS instrument with the graphite chamber (HGA-70) modification on a Perkin-Elmer Model 403 AAS:

Injection of 20 ml samples with Program 7, $T_1=30$ sec., $T_2=60$ sec., $T_3=30$ sec. Recorder Response 1, Recorder settings 0.5 A, 5 mV chart-paper speed 600/hr.

The calibration curve was prepared with Fc - COOH solutions in 0.1 N NaOH under the same instrument conditions as above.

EXAMPLE 3

Mercury-labelled Estradiol Hemisuccinate hapten (a) A tetrahydrofuran solution of estradiol hemisuccinate. $E_2(HS)$-COOH (300 mg. 0.775 m mole), p-aminophenyl mercuric chloride (277 mg, 0.775 m mole) and DCC, (dicyclohexyl diimide) (160 mg, 0.80 m mole) was stirred at room temperature for 36 hrs. The reaction mixture was filtered to remove the yellowish precipitate and the filtrate was evaporated to dryness to yield 618 mg of a solid residue.

Upon purification of 150 mg of above residue by column chromatography on silica gel and elution with chloroform/ethylacetate (3:1), the mercury-labelled amide, $E_2(HS)$-CONH-$C_6H_4$-HgCl, was obtained in a pure form having the following data: NMR($d_8$-THF) $\delta$(ppm) 7.3–7.9(4H,aromatic AA'BB' system). 6.5–7.2(3H, aromatic), 2.7 (4H, —$CH_2$—$CH_2$—), 0.95 (3H, angular $CH_3$).

(b) An alternative method for the synthesis of the amide $E_2(HS)$-CONH-$C_6H_4$-HgCl, was as follows: Estradiol hemisuccinate (200 mg, 0.55 m moles) in 2 ml dry DMF was mixed with triethylamine (0.1 ml) and isobutylchloroformate (0.16 ml) at −12° C. and stirred at this temperature for 20 min. After continuing stirring for 1 hr. at 0°, the reaction mixture was added in one portion to a solution of p-aminophenylmercuric chloride in dry DMF (2 ml). The mixture was stirred at room temperature for 48 hr. and then poured onto ice. The white precipitate was collected by filtration and air dried to yield 275 mg. This was purified by column chromatography as described in (a).

EXAMPLE 3A

The use of mercury-labelled estradiol hemisuccinate $E_2(HS)$-CONH-$C_6H_4$-HgCl to determine antibody-antigen interaction by AAS.

Step (i) - Calibration Curve

A stock solution of $E_2(HS)$-CONH-$C_6H_4$-HgCl was prepared by dissolving about 5 mg of the metallohapten in DMF (5 ml). The working solution (containing 15% DMF) was freshly prepared each day by making appropriate dilutions of the stock solution with 0.1 M phosphate buffer saline (PBS), pH 7.3. This working solution was used to prepare a calibration curve with a Perkin-Elmer atomic absorption spectrophotometer model 403 with graphite chamber attachment model HG-70 and deuterium background corrector, with the following experimental conditions: Program 3; drying time (100° C.), 60 sec; charring time, none; atomization time (2100° C.), 20 sec.; recorder response, 1; slit, 4; lamp current, 12 mA; carrier gas, argon; volume of injection, 30 μl.

The data for a typical calibration experiment follow: Stock solution: 5.3 mg $E_2(HS)$-CONH-$C_6H_4$HgCl in 5 ml DMF. Working solution: 0.2 ml stock solution + 0.55 ml DMF + PBS up to 5 ml. This provides a $6.22 \times 10^{-5}$M slution containing 12.47 μg Hg/ml. An additional 1:7 dilution provides the working solution with a concentration of 1.55 μg Hg/ml. Aliquots of this solution were added in increased volume to a 15% DMF/PBS solution, as shown in the table below.

Table 3A-1

| Run No. | Working Solution (μl) | 15% DMF/PBS (μl) | Molar Conc. (M × $10^{-7}$) | Hg Conc. (μg/ml) | Peak[a] Height (mm) |
|---|---|---|---|---|---|
| 1 | 5 | 115 | 3.23 | 0.064 | 57 |
| 2 | 15 | 105 | 9.70 | 0.192 | 121 |
| 3 | 20 | 100 | 12.9 | 0.256 | 146 |
| 4 | 30 | 90 | 19.4 | 0.384 | 204 |

[a]Average of duplicate measurements (S.D. < ± 5%).

The plot of the average peak height (mm) against the concentration (μg Hg/ml) gave a linear regression equation Y=456.7X+29.69 and a correlation coefficient $\gamma$=0.9991.

The calibration curve was run at the beginning of each working day to check the instrument settings and the stability of the working solution.

Step (ii) - Preparation of antisera and $\gamma$-globulins

The hapten, $E_2(HS)$-COOH was coupled to BSA by the mixed anhydride procedure using isobutylchloroformate in DMF. The degree of conjugation was determined by differential U.V. analysis. Rabbits were immunized by multiple subcutaneaus injection along the flank, nape and rump with an emulsion of complete Freund's adjuvant and the $E_2(HS)$-COOH-BSA conjugate. Bleeding was carried out prior to immunization (for normal serum) and at weekly intervals subsequent to immunization. Booster injections were given at regular six-weekly intervals. Sera from bleedings between boosters were pooled. Immuno-globulins were prepared from pooled antisera and normal sera by precipitation in ammonium sulfate followed by dialysis against 0.01 M PBS, pH 7.3. The γ-globulin solutions were divided into 1 ml portions in small vials and kept at −20° C., thawing the individual portions as needed before use.

Step (iii) - Preparation of Matrix-supported Anti $E_2(HS)$-COOH Antibodies

Cyanobromide - activated sepharose (Pharmacia Fine Chemicals) (1.0 g) was swollen and washed for 15 minutes with 200 ml of a solution of $10^{-3}$M HCl (pH=3). This gel was then mixed in a test-tube with anti-$E_2(HS)$-COOH antiserum (prepared from 6 ml of antiserum in a 0.1 M solution of phosphate buffer, pH=7.3, dyalized against 3×1 of a solution which was 0.1 M in NaHCO$_3$ and 0.5 M in NaCl, pH 8.2) and gently rotated end-over-end for 2 hrs. The gel was then washed and centrifuged successively with a solution of 0.1 M acetate buffer, then a solution of 0.1 M borate buffer (each being also 1 M in NaCl) until no ultraviolet absorption was observed at 280 nm. The solid phase was then resuspended in 10 ml of a 1 M ethanolamine solution, pH=8, and rotated end-over-end for 2 hrs. in order to deactivate any remaining active groups. This operation was then followed by several washing cycles and finally the solid was resuspended in 6 ml of a solution of 0.1 M phosphate buffer, pH=7.3. The amount of bound protein was calculated by substracting the amount of unbound protein removed in the washings (as measured at 280 nm) from that present in the original solution.

Step (iv) - Titration of the sepharose - supported Anti-$E_2(HS)$-COOH Antibodies Increasing amounts of $E_2(HS)$-CONH-C$_6$H$_4$-HgCl solution were added to a constant volume (30 μl) of the sepharose-supported anti-$E_2(HS)$-COOH antibodies (prepared in Step (iii) above) in polyethylene vials and the total volume made up to 120 μl with 15% DMF/PBS buffer. After incubation for 90 min at room temperature in a mechanical shaker, the vials were centrifuged for 10 min at 300 r.p.m. Aliquots (30 μl) were then drawn from the supernatant with an Eppendorf syringe and injected into the graphite chamber of the AA spectrometer. The concentration of the mercury found represented the free fraction of $E_2(HS)$-CONH-C$_6$H$_4$HgCl, not bound by the antibodies immobilized on the sepharose, and the fraction bound was obtained by difference.

The results obtained from such an experiment are given in the table below:

| Run No. | Volume of Hg-labelled Hapten added[a] (μl) | Molar conc. of Hg-labelled Hapten (M × 10$^{-7}$) | Total Hg Conc.[b] (μg/ml) | Peak Height Supernatant[c] (mm) | Free Hg. Conc. (μm/ml) | Bound (%) |
|---|---|---|---|---|---|---|
| 1 | 5 | 3.23 | 0.064 | 12 | 0.012 | 81.2 |
| 2 | 10 | 6.46 | 0.128 | 23 | 0.041 | 67.9 |
| 3 | 15 | 9.7 | 0.192 | 40 | 0.085 | 55.7 |
| 4 | 20 | 12.9 | 0.256 | 60 | 0.119 | 53.5 |
| 5 | 25 | 16.2 | 0.320 | 73 | 0.171 | 46.5 |
| 6 | 30 | 19.4 | 0.384 | 86 | 0.204 | 46.8 |

[a]A constant volume of 30 μl antibody-sepharose suspension used throughout.
[b]Final total volume: 120 μl
[c]Linear regression equation of calibration curve: Y = 384.3x + 7.4 (where x = μg Hg/ml)

EXAMPLE 4

Mercury-labelled Estrone oxime-0-carboxymethyl hapten

Estrone oxime - 0 - carboxymethyl, $E_1$(OX)-COOH, (200 mg, 0.583 m mole), p-aminophenylmercuric chloride (191 mg), DDC (121 mg, 0.587 m mole) in freshly distilled tetrahydrofuran (6 ml) were stirred at room temperature for 20 hr. The reaction mixture was filtered to remove the precipitate and the filtrate was evaporated to dryness to yield 345 mg of a solid residue. Chromatography on silica and elution with chloroform/methanol (99:1) yielded 100 mg of pure amide; $E_1$-(OX)-CONH-C$_6$H$_4$HgCl having the following data:

NMR spectrum (d$_8$-THF), δ(ppm) 7.4–7.8 (4H, aromatic, AA'BB'system), 6.5–7.3 (3H, aromatic), 4.6 (2H,—OCH$_2$—), 0.9 (3H, angular CH$_3$). The same amide, $E_1$(OX)-CONH-C$_6$H$_4$HgCl was prepared by the mixed anhydride method using isobutyl-chloroformate, as described in (b) of Example 3.

EXAMPLE 5

Mercury-labelled Estradiol haptens

This Example involves the following steps:
Step (i)

A solution of estradiol (1.0 g, 3.67 m moles) and mercuric acetate (1.1 g, 3.45 m moles) in methanol (20 ml) was refluxed for 2.5 hr and then stirred at room temperature for 20 hrs. After addition of more mercuric acetate (1.1 g, 3.45 m moles) the reaction mixture was refluxed for 2 hr., cooled to room temperature and filtered to separate the solid and liquid phases, (a) and (b) respectively. Each phase we worked up separately as follows:

(a) The solid phase was dissolved in 10 ml of a mixture of methanol/chloroform/methylene chloride (1:1:1) mixed with a solution of lithium chloride (400 mg) in methanol (3 ml) and stirred at room temperature for 20 hrs. The solvent was evaporated off in vacuum (obtained by a water pump) and the residue dissolved in ethyl acetate (25 ml). The solution was extracted with water (3×50 ml) to remove inorganic chlorides, dried over MgSO$_4$ and the solvent removed to yield 0.6 g of a solid product. Thin layer chromatography (T.L.C.) showed the presence of three new compounds chloromercuriestradiol derivatives in addition to a small amount of unreacted estradiol.

(b) The liquid phase was mixed with lithium chloride (400 mg) and stirred at room temperature for 20 hrs. A white inorganic precipitate was deposited and was separated by filtration. The filtrate was evaporated to dryness and the residue was taken up in ethyl acetate, washed with water and dried over $MgSO_4$. The organic solvent was removed in vacuum to yield a solid, which by T.L.C. was shown to have the same composition as in (a) above.

Step (ii)

Separation of the chloromercuriestradiol derivatives was achieved through acetylation of the hydroxyl functions, chromatograpy on silica, to obtain the pure components and hydrolysis of the acetates to regenerate the pure chloromercuriestradiol derivatives. A typical procedure was as follows: the mixture obtained in (a) or (b) in Step (i) above (0.6 g) was refluxed in acetic anhydride (3 ml) and dry pyridine (15 ml) for 2 hrs. After cooling to room temperature, the reaction mixture was added dropwise to 200 ml of magnetically-stirred ice-cold water. The white precipitate was filtered off and dried to yield 0.59 g of a glassy residue. Chromatography on silica, eluting with benzene and then with benzene/chloroform, yielded first estradiol acetae (88 mg) followed by 2-chloromercuri estradiol diacetate (190 mg), then 4-chloromercuriestradiol diacetate and lastly 2,4-(bis-chloromercuri estradiol diacetate. The three chloromercuridiacetate derivatives could be characterized by their typical N.M.R. spectrum, in particular that of the benzene-ring protons, for determination of position and degree of substitution.

Step (iii)

Hydrolysis of each one of the separated chloromercuridiacetates yielded the respective chloromercuriestradiol derivative, namely 2-chloromercuriestradiol, 4-chloromercuriestradiol, and 2,4-(bis-chloromercuri)-estradiol.

A typical hydrolysis experiment follows:

A solution of 4-chloromercuriestradiol diacetate (65 mg) in a 5% by wt potassium hydroxide in methanol (20 ml) and lithium chloride (12 mg) was stirred at room temperature for 1 hr. After evaporation of the methaol in vacuum (obtained by a water pump) the residue was mixed with water (50 ml), some lithium chloride was added and the mixture extracted with chloroform ($2\times25$ ml) and then with ethyl acetate ($3\times20$ ml). The organic solvent phase was then washed with water, dried over $MgSO_4$ and evaporated to yield 48 mg of 4-chloromercuriestradiol.

Analysis: Calculated for $C_{18}H_{23}O_2HgCl$: C, 42.60; H, 4.57%. Found: C, 42.60; H, 4.85%.

NMR Spectrum ($d_8$-THF): $\delta$(ppm) 6.7–7.3 (2H aromatic, AB system) 0.9 (3H, singled, angular $CH_3$).

Step (iv)

Additional proof of structure of the chloromercuric derivatives was obtained by transformation into the respective iodo-estradiol derivatives:

The chloromercuriestradiol mixture obtained in (a) above (0.6 g) was suspended in chloroform (20 ml) and iodine (0.3 g) was added under stirring at room temperature. After stirring for 20 hours at room temperature, the reaction mixture was filtered to remove the red precipitate and the chloroform filtrate was extracted with a potassium iodide aqueous solution until all the free iodine was removed. The chloroform phase was then dried over $MgSO_4$ and evaporated to yield 454 mg of a solid residue. This was chromatographed on a silica gel column, eluting with carbon tetrachloride and carbon tetrachloride-diethyl ether mixtures. The following compounds, in order of elution were isolated in a pure form:

(i) 2,4-diiodoestradiol (42 mg), NMR ($CCl_4$) $\delta$(ppm) 7.7 (1H, aromatic), 0.9 (3H, angular $CH_3$):

(ii) 2-iodoestradiol (31 mg), NMR ($CCl_4$) $\delta$(ppm) 7.5 (1H, aromatic), 6.5 (1H, aromatic), 0.9 (3H, angular $CH_3$);

(iii) 4-iodoestradiol (60 mg), NMR ($CCl_4$) $\delta$(ppm) 6.6–7.3 (2H, aromatic, AM system), 0.8 (3H, angular $CH_3$).

The balance of material eluted from the column consisted of mixtures of the above three compounds.

EXAMPLE 5A

Mercury-labelled Estroil Haptens

The procedure described for estradiol in Example 5 was also applied to estriol as follows: Mercuric acetate (0.635 g, 2 m moles) was added to a solution of estriol (0.575 g, 2 m moles) in methanol (20 ml). The mixture was refluxed for 4 hr. and then stirred at room temperature for 12 hr. Addition of $CHCl_3$ (20 ml) and $CH_2Cl$ (20 ml) to the reaction mixture produced a clear solution, which was then treated with LiCl (0.2 g) in methanol (3 ml). After stirring at room temperature for 12 hr, the organic solvents were removed in vacuum and the solid residue (1.26 g) was washed with water ($3\times25$ ml). The combined aqueous washings were extracted with ethyl acetate ($3\times25$ ml), to recover any dissolved estriol derivatives. The residue obtained after evaporation of the combined ethyl acetate extracts was combined with the solid residue obtained above and the mixture was treated as in steps (ii) and (iii) of Example 5 in order to separate the chloromercury estriol derivatives. If on the other hand the iodoestriol derivatives were desired, the solid residue obtained above was dissolved in THF and titrated dropwise with a solution of iodine (0.5 g) in $CHCl_3$ (50 ml) until the iodine colour in the reaction mixture remained stable. After evaporation of the solvent the residue, which was a mixture of 2-iodoestriol, 4-iodoestriol and 2,4-diiodoestroil, was chromatographed on a silica gel column to give pure 2,4-diiodoestroil (0.1 g) and a mixture of 2-iodo- and 4-iodoestriol (0.32 g). The two monoiodoestroil derivatives could be separated if desired, by repeated chromatograpy. The NMR spectra of the three compounds, in the aromatic protons region, were identical to those described for the estradiol derivatives in Example 5.

The two methods given in Example 5 and 5A could provide a very convenient way for preparing pure radioactive iodine derivatives of estradiol and estriol.

EXAMPLE 6

Iron-labelled Estradiol hemisuccinate hapten $E_2(HS)$-$CONH$-$CH_2Fc$

Step (i) - Synthesis of Estradiol -17$\beta$-succinate-N-succinimide ester

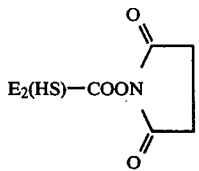

DCC (58 mg, 0.28 m mole) was added to an ice-cooled solution of estradiol-17β-hemisuccinate, $E_2$(HS)-COOH, (93 mg, 0.25 m mole) and N-Hydroxysuccinimide, NHS, (30 mg, 0.25 m mole) in dry, freshly distilled THF (4 ml). The reaction mixture was stirred for 3 hrs. at 0° and then overnight at room temperature. After removing the precipitate dicyclohexyl urea by filtration, the THF filtrate was evaporated to dryness to yield 120 mg of a white solid which was shown by IR and NMR spectra to be the expected active ester

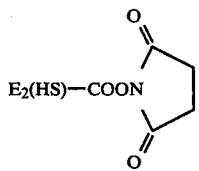

This was used in the next step without further purification.

Step (ii)

A solution of the active ester

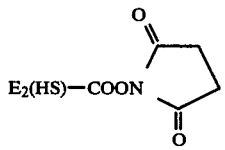

(120 mg), about 0.25 m mole and ferrocenylmethyl amine, Fc-$CH_2NH_2$, (55 mg, 0.25 m mole) in dry freshly distilled THF (4 ml) was magnetically - stirred at room temperature for 20 hrs. The mixture was filtered to remove some precipitated material and the THF filtrate was evaporated to dryness to yield a white solid residue. This was dissolved in ethyl acetate (10 ml) and the solution was washed with water (2×10 ml). The organic solvent phase was dried over $MgSO_4$ and evaporated to yield 160 mg of a solid residue. This was purified by column chromatography on a 10% deactivated basic alumina (7 g). Elution with benzene-chloroform (4:1) yielded 55 mg (40% yield) of a pure compound, m.p. 140°-143°, shown by I.R., NMR and high resolution mass spectrum analyses to be the amide $E_2$(HS)-CONH-$CH_2$-Fc.

IR(CHCl$_3$) $\nu$(cm$^{-1}$): 1720 (vs)- 1660 (vs): 1170 (s): 1100 (s): 1000 (m).

NMR(CDCl$_3$) $\delta$(ppm): 7.3–6.8 (aromatic 3H): 4.3(ferrocenyl 9H) 0.8 (angular methyl 3H).

Molecular ion (high resolution mass spectrum, m/e) 569.2238 which analyzed for $C_{33}H_{39}O_4$ N Fc.

EXAMPLE 6A

The use of iron-labelled estradiol hemisuccinate, $E_2$(HS)-CONH-$CH_2$Fc, to determine antibody-antigen interaction by AAS.

Step (i) - Calibration Curves

A procedure similar to that described in Example 3A-Step (i) was followed. The labelled hapten, $E_2$(HS)-CONH-$CH_2$Fc, was dissolved in DMF to prepare a stock solution of 1 mg/ml. Dilutions were made with buffer solutions (0.05 M sodium citrate buffer, pH 7.3, or 0.01 M potassium phosphates buffer, pH 7.3) to obtain working standard solutions containing 15% DMF. The calibration curves were prepared: (a) by the method of standard addition: 90 μl of stock solution were diluted to a volume of 10 ml and then 30 μl portions were injected in the AAS, to get a working range of 50–300 ng Fe/ml; (b) by the usual dilution method whereby 30,60,90 and 120 μl of a suitably concentrated solution were made up, with buffer solution, to a total volume of 120 μl. Each standard concentration was prepared in duplicate and each AA measurement was carried out in duplicate or triplicate with Perkin-Elmer instrument, model 403 with graphite chamber attachment model HG-70 and deuterium background correcter. The experimental conditions were: Program 7; drying time (100° C.), 40 sec.; charring time (1100° C.), 90 sec.; atomization time (2400° C.), 10 sec.; slit, 3; lamp current, 20 mA; carrier gas, argon; recorder response, 1; 0.25 A, 20 mV, chart speed 2 cm/min. The following data were obtained for the standard addition procedure for two typical calibration experiments, one with solutions made in triply distilled water with 15% DMF (Table 6A-1) and the second with solutions made in 0.01 M PBS with 15% DMF (Table 6A-2).

Table 6A-1

| Run No. | Molar conc. of Fc-labelled Hapten (M × 10$^{-7}$) | Fe. conc. (ng/ml) | Peak[a] Height (mm) | Average of duplicates A and B (mm) |
|---|---|---|---|---|
| 1A | 0[b] | 0 | 17.6 ± 1.5 | 16.8 |
| 1B | 0 | 0 | 16.0 ± 0 | |
| 2A | 1.98 | 11.0 | 39.7 ± 2.5 | 39.5 |
| 2B | 1.98 | 11.0 | 39.3 ± 1.1 | |
| 3A | 3.95 | 22.1 | 61.0 ± 2.6 | 60.0 |
| 3B | 3.95 | 22.1 | 59.0 ± 1.7 | |
| 4A | 5.93 | 33.2 | 80.5 ± 2.1 | 80.9 |
| 4B | 5.93 | 33.2 | 81.3 ± 3.0 | |
| 5A | 7.90 | 44.2 | 101.0 ± 1.4 | 100.6 |
| 5B | 7.90 | 44.2 | 100.3 ± 2.5 | |

[a]Average of triplicate measurement ± S.D.
[b]Blank solution: triply distilled water with 15% DMF.

The plot of the average peak height of duplicates (mm) against the concentration (ng Fe/ml) gave a linear regression equation Y=1.889x+17.80 and a correlation coeffient r=0.9997.

Table 6A-2

| Run No. | Molar conc. of Fe-labelled Hapten (M × 10$^{-7}$) | Fe conc. (ng/ml) | Peak[a] Height (mm) | Average of duplicates A and B (mm) |
|---|---|---|---|---|
| 1A | 0[b] | 0 | 41.0 ± 1.7 | 41.0 |
| 1B | 0 | 0 | 41.0 ± 1.0 | |
| 2A | 1.98 | 11.0 | 65.0 ± 2.0 | 65.3 |
| 2B | 1.98 | 11.0 | 65.5 ± 2.1 | |
| 3A | 3.95 | 22.1 | 78.7 ± 1.5 | 80.1 |
| 3B | 3.95 | 22.1 | 81.5 ± 2.1 | |
| 4A | 5.93 | 33.2 | 102.0 ± 3.0 | 99.8 |
| 4B | 5.93 | 33.2 | 97.5 ± 4.9 | |
| 5A | 7.90 | 44.2 | 113.5 ± 4.9 | 119.5 |
| 5B | 7.90 | 44.2 | 125.5 ± 3.5 | |

[a]Average of triplicate measurements ± S.D.
[b]Blank solution: 0.01 M of PBS with 15% DMF.

The plot of the average peak height of duplicates (mm) against the concentration (ng Fe/ml) gave a linear regression equation Y=1.731x+42.88 and a correlation coefficient r=0.9977.

Step (ii) - Titration of the sepharose-supported Anti-E2(HS)-COOH

In order to carry out the assay, several factors were checked using the antisera obtained as described in Example 3A-Step (ii), and the sepharose-immobilized antibodies prepared as in Example 3A-Step(iii). For the determination of non-specific absorption by the sepharose, a sepharose preparate was obtained according to the procedure of Example 3A-Step (iii), except that γ-globulins of normal rabbit serum (NRS) were used instead of the anti-E2(HS)-COOH antibodies.

A constant volume (60 μl) of the suspension of sepharose-bound antibodies (or NRS γ-globulins) was Vortex-mixed with appropriate volumes of known concentrations of E2(HS)-CONHCH2Fc and allowed to incubate for 30 min. at room temperature, with repeated Vortex-mixing every 10 min. The mixture was then centrifuged for 1 min. at 3000 r.p.m. Aliquots (30 μl) from the supernatant were extracted with an Eppendorf pipette and injected into the graphite chamber of the AA instrument.

The results, including calibration standards, with and without sepharose suspensions, are brought together in Table 6A-3. In this table the peak height results are given after appropriate substraction for the blank signals, so that the calibration curve intersects the origin.

Table 6A-3

| Run No. | Molar conc. of Fe-labelled Hapten (M × 10$^{-7}$) | Fe conc. (ngl ml) | NRS-γ-globulins (μl) | Anti-E2(HS)CO2H γ-globulins (μl) | Peak height (mm) |
|---|---|---|---|---|---|
| Blank | — | — | — | — | 0 |
| 1 | 17.9 | 100 | — | — | 32 |
| 2 | 17.9 | 100 | 60 | — | 33 |
| 3 | 35.8 | 200 | — | — | 60 |
| 4 | 35.8 | 200 | 60 | — | 58 |
| 5 | 53.7 | 300 | — | — | 87 |
| 6 | 9.16 | 51 | — | 60 | 9.5 |
| 7 | 18.3 | 102 | — | 60 | 12.5 |
| 8 | 27.5 | 154 | — | 60 | 16.0 |
| 9 | 36.6 | 205 | — | 60 | 22.5 |
| 10 | 45.8 | 256 | — | 60 | 35.0 |
| 11 | 55.1 | 307 | — | 60 | 46.5 |

Plotting the above data on a graph permitted the calculation of the molar concentration of antibody sites (5.01×10$^{-6}$M) on the sepharose and the binding constant ($K_{av}$=3.44×10$^{-5}$ M$^{-1}$) of the labelled hapten.

Step (iii) - Inhibition and Cross-reaction Experiments with E2(HS)-CONH-CH2-Fc.

A fixed volume (30 μl) of a solution of iron-labelled estradiol hemisuccinate, E2(HS)-CONH-CH2Fc, of suitable concentration (selected from the results obtained in Step (ii) above) was mixed with a constant volume (30 μl) of solutions of various concentrations of unlabelled hapten, estradiol hemisuccinate (or estrone-17-(0-Carboxymethyl)oxime, E1(Ox)-COOH). This mixture was added to a constant volume (60 μl) of the sepharose-bound antibodies, Vortex-mixed for 1 min. and allowed to incubate at room temperature for 30 min. The Vortex-mixing was repeated at intervals of 10 min. The assay mixture was then centrifuged for 1 min. at 3000 r.p.m. Aliquots (30 μl) were extracted with an Eppendorf pipette and injected into the graphite tube of the AA instrument. The following controls were taken through the same procedure to determine specificity: (a) a suspension of sepharose-bound antibodies without addition of metal-labelled hapten; (b) the mixtures of metal-labelled and non-labelled haptens, without addition of the sepharose-bound antibodies; (c) the mixture of metal-labelled and non-labelled haptens with addition of sepharose-bound γ-globulins of normal rabbit serum.

The inhibition values obtained with the two haptens are given in Table 6A-4.

Table 6A-4

| Inhibition of E2(HS)—CONH—CH2Fc (27.5 × 10$^{-7}$ M) | | | |
|---|---|---|---|
| [E2(HS)—COOH] (M × 10$^{-7}$) | Inhibition (%) | [E1(OX)—COOH] (M × 10$^{-7}$) | Inhibition (%) |
| 3.6 | 8.5 | 3.75 | 0.5 |
| 7.2 | 17.5 | 7.5 | 3.0 |
| 15.0 | 21.5 | 15.0 | 6.5 |
| 36.0 | 43.5 | 37.5 | 9.5 |
| 72.0 | 48.0 | 75.0 | 25.5 |
| 150.0 | 56.0 | 150.0 | 50.5 |
| 300.0 | 63.5 | | |

EXAMPLE 7

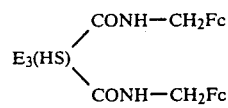

Iron-labelled Estriol -bis-hemisuccinate hapten

Step (i)

By following the same procedure as described in Example 6 (Step (i)) with estriol-16α,17β-bishemisuccinate (496 mg, 1 m mole), N-hydroxysuccinimide (230 mg, 2 m moles) and DCC (450 mg, 2.2 m moles) obtained the active bis-ester,

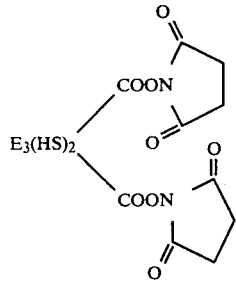

550 mg (81%) yield m.p. 90°–95° C.

Step (ii)

The active bis-ester obtained above (130 mg, 0.19 m mole) and ferrocenyl methylamine (81 mg, 0.38 m mole) were reacted by the procedure given in Example 6 (Step (ii)) to yield, after purification by column chromatography and then by preparative TLC, 60 mg (~30% yield) of the bis-amide

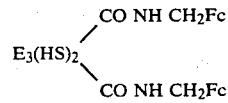

I R(CHCl3); ν(cm$^{-1}$): 1730 (vs):1615 (vs):1500 (s):1170 (s):1110 (m):1000 (m).

NMR(CDCl3) ν(ppm): 7.3–6.7 (aromatic 3H); 4.26 (bis-ferrocenyl, 18H):0.8 (angular methyl, 3H).

EXAMPLE 8

Iron-labelled 1,3,5-Estratriene-3-Ol-17 amine hapten E₁-NHCO CH₂CH₂CO-Fc

Step (i) - Synthesis of 4-Keto-4-ferrocenyl butanoate-N-succinimide ester 4-keto-4-ferrocenyl butanoic acid (prepared by a Friedel-Crafts reaction with succinic anhydride on ferrocene) (286 mg), (1 m mole) and N-hydroxysuccinimide (115 mg, 1 m mole) were reacted following the procedure described in Example 6 (Step (i)) to yield 300 mg (78% yield) of the active ester

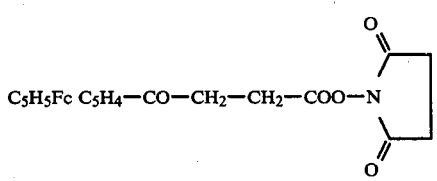

IR(CHCl₃) ν(cm⁻¹): 1815; 1790; 1745; 1715; 1660; 1180; 1070.

NMR(CDCl₃) δ(ppm): 4.88(C₅H₄,2H); 4.50(C₅H₄,2H); 4.25(C₅H₅,5H); 3.08(—CH₂—CH₂—,4H); 2.87 (succinimide ring, 4H)

This compound can serve as a reagent for metal-labelling haptens which have amino-functional groups, as shown in Step (iii) below.

Step (ii) - Synthesis of 1,3,5-Estratriene-3-Ol-17-amino E₁-NH₂

Cobalt chloride hexahydrate, CoCl₂.6H₂O, (670 mg, 2.8 m mole) was added to a solution of estrone oxime (390 mg, 1.37 m mole) in methanol (80 ml) and the solution stirred at room temperature until homogeneous. Sodium borohydride (580 mg) was then added over a period of 20 minutes. During this addition the solution turned black and a vigorous evolution of hydrogen was observed. After stirring for an additional hour at room temperature, the reaction mixture changed colour to yellowish-brown. The solvent was evaporated in vacuo and the resulting residue extracted with several portions of warm ethyl acetate. The combined extracts were evaporated in vacuum to yield 359 mg of the amine E₁-NH₂ as a white crystalline material which had a m.p. of 190°–193°. Above 193° the material became crystalline again which then melted with decomposition at 235°–238°.

NMR(CD₃OD), δ(ppm): 7.25–6.6(3H, aromatic); 0.7(3H, angular CH₃).

Step (iii) - Synthesis of E₁-NH CO CH₂CH₂CO Fc

A solution of E₁-NH₂ prepared in Step (ii) above, (50 mg, 0.18 m mole) in freshly distilled dioxane (3 ml) was added to a magnetically stirred solution of the active ester, prepared in Step (i) above, (50 mg, 0.13 m mole) in dioxane (3 ml). Stirring was continued, at room temperature, for 30 minutes and the solvent was evaporated in vacuum. The residue was extracted with chloroform. The combined extracts were washed with water, dried over MgSO₄ and evaporated to yield 86 mg of a brownish residue. This was purified by preparative TLC resulting in 31 mg (45% yield) of the amide E₁-NH-CO-CH₂-CH₂-CO Fc, m.p. 228°–230°.

IR(CHCl₃), ν(cm⁻¹): 1660(s):1990(m):1100(m); 1005(m)

NMR(CDCl₃) δ(ppm): 7.0–6.6 (3H, aromatic); 4.7–4.2 (9H,ferrocenyl); 0.7 (3H, angular CH₃).

EXAMPLE 9

Chromium-labelled Estradiol hemisuccinate hapten E₂(HS)-CO NH-(acac)Cr(acac)₂.

A solution of monoamino-tris-acetylacetonate-chromium (acac)₂-Cr (acac)-NH₂ (prepared according to Collman and Yamada, J. Org. Chem., 28, 3017 (1963), (400 mg, 1.1 m mole), estradiol hemisuccinate, E₂(HS)-COOH, (350 mg, 0.95 m mole), DCC (210 mg, 1.05 m mole) in methylene chloride (30 ml) was magnetically stirred at room temperature for 18 hrs. After removing the precipitated urea by filtration, the solvent was evaporated. The residue was redissolved in a small amount of benzene and after addition of petroleum ether an additional amount of urea was precipitated which was removed by filtration. After removal of the benzene-petroleum ether solvents, the residue was extracted several times with acetone. The combined acetone extracts were evaporated to yield 376 mg (58% yield) of the crude amide which ws purified by preparative TLC to yield 100 mg (15% yield) of the desired pure amide, E₂(HS)-CONH-(acac)Cr(acac)₂.

I.R.(CHCl₃) ν(cm⁻¹): 1740 (s):1670 (s):1580 (vs):1520 (vs):1370 (vs):1280 (m):1020 (m):920 (m).

EXAMPLE 10

Copper - and Palladium-labelled Estradiol hemisuccinate hapten

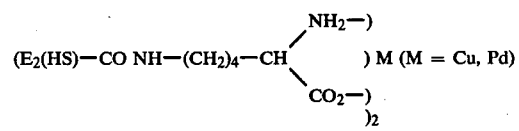

A solution of the NHS active ester of estradiol hemisuccinate, prepared as in Step (i) of Example 6, (300 mg, 0.63 m mole) in THF (8 ml) was added to a saturated aqueous solution of NaHCO₃ (8 ml) containing bis-lysinato copper (223 mg, 0.63 m mole) prepared according to Brubaker and Busch, Inorg. Chem., 5, 2110 (1966). A two-phase liquid system resulted with the blue-coloured aqueous solution being the lower phase. After magnetically stirring the reaction mixture at room temperature for 2 hrs. the blue colour passed to the top phase (THF). The mixture was transferred to a separating funnel and the blue THF layer ws collected and evaporated to dryness. The pale blue residue was extracted with ethylacetate to remove any unreacted steroid. The remaining solid was shown by TLC to be a pure material and the infra red spectrum agreed with the expected product in which the terminal NH₂ group of the lysine moieties had reacted with the active ester to form the peptide link of

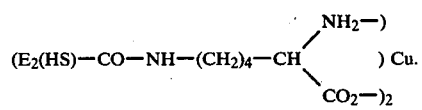

By similar procedures it was possible to prepare the palladium analog.

EXAMPLE 11

Cobalt-labelled Estradiol hapten

Step (i)

The N-carbobenzoxy derivative of aspartic acid was transformed into the anhydride by the procedure of Le Quense and Young, J. Chem. Soc., 1954 (1951).

Step (ii)

The anhydride prepared in Step (i) above, (0.76 g) and estradiol (0.83 g) were refluxed in pyridine (10 ml) for 4 hr. After removal of the solvent, the residue was extracted several times with CHCl₃ to remove unreacted estradiol. The remaining solid was dissolved in a very small amount of DMF and reprecipitated with acetone to yield 1.0 g of solid which was shown by NMR and IR to be

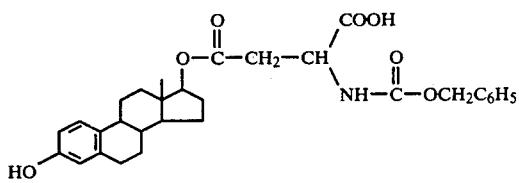

Step (iii)

Hydrogenolysis of the compound obtained in Step (ii) above with palladium catalyst removed the carbobenzoxy group to yield the estradiol substituted aspartic acid

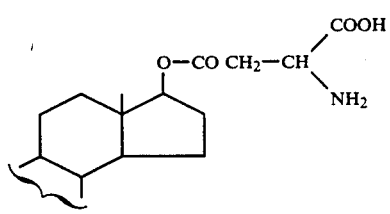

Step (iv)

This amino acid derivative can be reacted with suitable metal derivatives to yield amino acid complexes.

For example, reaction of carbonato-bis-ethylene-diamine cobalt chloride, (Co en₂ CO₃)Cl, with above amino acid brings about displacement of the CO₃ group and formation of the complex

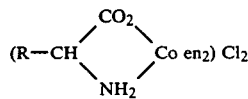

Similar procedures have been carried out with other suitable amino acids, such as cystein or glutamic acid.

EXAMPLE 12

Synthesis of Iron-labelled Cannabinoid-Metallohapten

Step (i) - Preparation of an active ester derivative of 1 - carboxy - Δ⁶ - THC 1-carboxy-Δ⁶-THC (74 mg, 0.22 m mole) and N-hydroxy succinimde (30 mg, 0.22 m mole) in dry, freshly distilled THF (5 ml) were mixed for 3 hr. under stirring and cooling with a solution of DCC (50 mg, 0.24 ml) in THF (3 ml). After standing at room temperature for 15 hr., the reaction mixture was filtered to remove the precipitated dicyclohexyl urea and the filtrate was used in the next step without any other work-up.

Step (ii) - Reaction of active ester of 1-carboxy-Δ⁶-THC with aminomethylferrocene.

Aminomethylferrocene, $C_5H_5FeC_5H_4CH_2NH_2$, (47 mg, 0.22 m mole) was added to the THF solution of the active ester of 1-carboxy-Δ⁶-THC, obtained in Step (i) above. The mixture was stirred at room temperature for 20 hrs. and then at 60° for 3 hrs. After evaporation of the solvent, the solid residue was dissolved in diethyl ether (10 ml) and washed twice with 10 ml water. After drying the organic phase over Mg SO₄ and evaporation of the solvent there remained 158 mg of a crude mixture. Separation by preparative TLC and elution with chloroform-ethylacetate (1:1) yielded 45 mg (45% yield) of the pure yellow-crystalline amide, m.p. 73°-76°, $C_5H_5FeC_5H_4CH_2NH-CO-(Δ^6-THC)$.

I.R.(CHCL₃) $\nu(cm^{-1})$: 1720 ($\nu$); 1660 (m); 1625 (vs); 1580 (m) 1180-1280 (brs) 1105 (m); 1000 (m); 910 (vs).

NMR(CDCL₃) δ(ppm): 6.86 (vinylic H); 6.27 (aromatic 2H) 4.20 (ferrocenyl 9H); 3.4 (br,-CH₂-N)

EXAMPLE 13

Synthesis of Manganese-labelled Barbiturate-Metallohapten

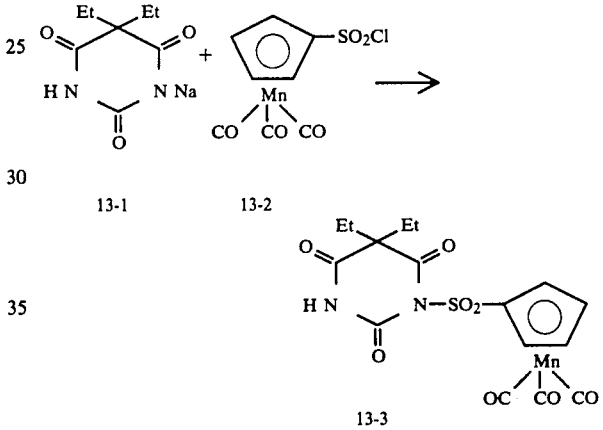

A solution of sodium barbital (0.144 g, 0.7 m moles), 13-1 and cymantrenyl sulfonyl chloride (0.214g, 0.7 m moles), 13-2, in methanol (40 ml) was refluxed for 2 hrs and then stirred at room temperature for 36 hrs. After evaporating the solvent, the residue was extracted with chloroform (3×10 ml). The combined CHCl₃ extracts were evaporated and the residue was purified on a preparative TLC plate (alumina). Elution with chloroform methanol (9:1) yielded the desired product, 13-3, in the top streak (R$_f$≈0.9) (60 mg)

IR(CHCl₃) $\nu(cm^{-1})$: 2050 (vs); 1950 (vs) (typical metal carbonyl) 1740 (vs); 1690 (vs) (barbiturate carbonyls).

NMR(CDCl₃) δ(ppm) 4.9 and 5.6 (cyclopentadienyl 4H); 0.9 (triplet) (2CH₃ groups); 2.0 (quartet) (2CH₂ groups).

EXAMPLE 14

Synthesis of Chromium-labelled Barbiturate Metallohapten

Step (i) - Synthesis of 1-carboxymethyl-5,5-diethyl barbituric acid and 1,3-bis(carboxymethyl)-5,5-diethyl barbituric acid.

A solution of sodium barbital (4.63 g, 22.5 m mole) and methyl chloroacetate (3.69 g, 40.0 m mole) in methanol (50 ml) and dimethylsulfoxide (10 ml) was refluxed for 2 hr. The methanol solvent was removed in vacuum and the remaining solution was diluted with water (50 ml), whereupon a gummy material separated out. After decanting the aqueous layer, the gummy residue was triturated with several portions of 1N NaOH solution. After collecting and combining the alkaline layers, the insoluble residue (0.92 g) was dried and found, by IR and NMR spectra, to be the dimethyl ester of the disubstituted 1,3-bis(carboxy methyl)-5,5-diethyl-barbituric acid. (NMR(CDCl₃) δ(ppm) 4.85 (singlet,-N-CH₂-); 3.8 (singlet, -OCH₃); 2.1 (quartet, -CH₂ of ethyl groups); 0.9 (triplet, CH₃ of ethyl groups).

The alkaline washings were acidified and extracted with methylene chloride. The residue obtained after evaporation of the CH₂Cl₂ solvent was chromatographed on a silica gel column to obtain the monosubstituted ester, 1-carboxymethyl-5,5-diethylbarbituric acid. The NMR spectrum was the same as for the diester derivative, except for the integration pattern (which agreed with monosubstitution) and the additional absorption at δ 10.5 for the -NH proton.

The two compounds, the diester and the monoester were hydrolyzed to the free carboxylic acids by refluxing for 3-4 hrs. in 20% HCl solution, and work up in the usual way, IR and NMR spectra confirmed the structures of the free (carboxymethyl) derivatives.

Step (ii) - Synthesis of active esters with N-hydroxysuccinimide and reaction with (acac)₂Cr(acac)-NH₂.

(A) N-hydroxysuccinimide (0.46 g, 3.98 m mole) and DCC (1.1 g, 5.4 m mole) were added to a THF solution of the bis-(carboxymethyl) derivative obtained in Step (i) above from the hydrolysis of 0.61 g (1.8 m mole) of the diester. The reaction mixture was stirred at room temperature for 15 hrs, filtered to remove the precipitated urea derivative and the solvent from the filtrate was stripped off. The crude residue (~0.25 m mole) was dissolved in methylene chloride and after addition of (acac),Cr(acac)NH₂ (0.14 g, 0.38 m mole) the reaction mixture was stirred at room temperature for 36 hrs. The precipitate formed in the reaction was filtered off and the residue obtained upon evaporation of the solvent from the filtrate was purified by chromatography on a silica gel column to yield 30 mg of the pure material, 14-1 (single spot on TLC and IR(CHCl₃) ν(cm⁻¹) 1740, 1690, 1580, 1450, 1380.

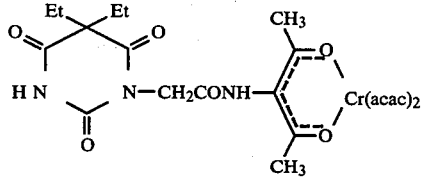

EXAMPLE 15

Synthesis of Platinum-labelled Estrone-hapten

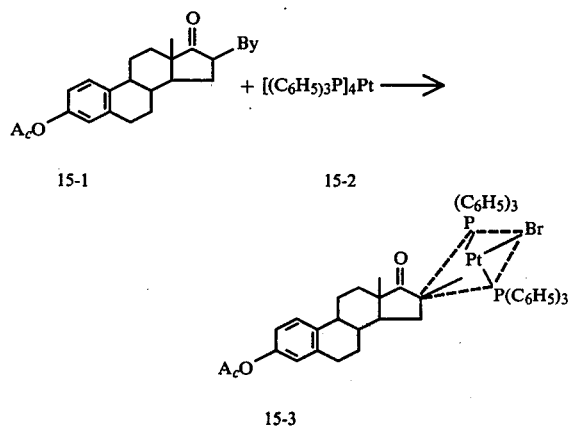

A solution of tetrakis (triphenylphosphine) platinum, 15-2, (0.25 g, 0.2 m moles) and 16-bromo estrone acetate, 15-1, (0.1 g 0.26 m moles) in benzene (8 ml) was refluxed under nitrogen for 2 hr. The solvent was then removed with a stream of nitrogen and the residue was washed with several portions (6×20 ml) of hot petroleum ether to remove free triphenylphosphine. The residue was then dissolved in methanol, filtered and the filtrate evaporated in vacuum. The residue was recrystallized twice from methylene chloride/hexane to yield 70 mg (32% yield) of colourless crystals, melting, with decomposition, at 265°-267° C., and showing a single spot on TLC (R$_f$~0.57, silica gel, 2% MeOH in

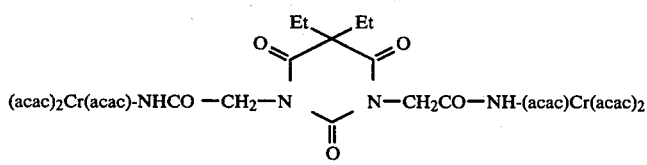

(B) The procedure described in (A) above was repeated with the mono-carboxymethyl derivative (0.13 g, 0.5 m mole), except that the final chromatographic purification was done on a florisil column (60-100 mesh) to yield 50 mg of the pure material 14-2 (single spot on TLC and IR(CHCl₃), ν(cm⁻¹) 1740, 1640, 1580, 1520, 1380.

CHCl₃). IR(KBr disc),ν(cm⁻¹), 690(vs), 740 (vs), 1000(m), 1090(vs), 1165(m), 1190l (m), 1210(s), 1435(vs), 1485(vs), 1745(vs), 1765(s), 2910(s), 3050(s). NMR(CD₂Cl₂),δ(ppm): 7.3 broad, (C₆H₅)₃P and steroid aromatic protons); 2.25(singlet, CH₃CO), 1.5(singlet, angular CH₃) and broad resonances between 3.0 and 0.5 due to the aliphatic steroid protons.

EXAMPLE 16

Synthesis of Manganese-labelled Estrone Hapten

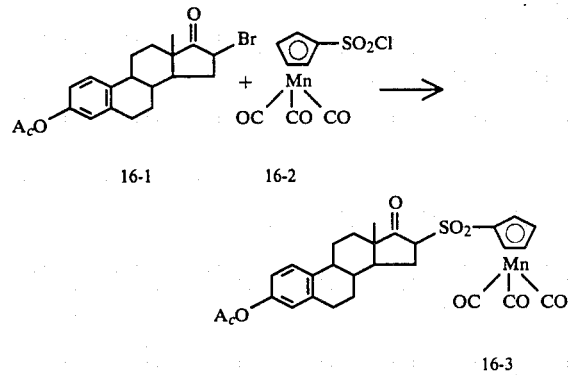

A solution of 16-bromo estrone acetate, 16-1 (55 mg, 0.014 m mole) and sodium cymantrenylsulfinate, 16-2, (55 mg, 0.019 m mole) in DMF (1 ml) was refluxed for 4 hr. After cooling and addition of water (5 ml) the reaction mixture was extracted with ethyl acetate (3×10 ml). The organic layer was dried (MgSO$_4$) and evaporated in vacuum. The residue was purified by preparative TLC to yield 23 mg of the estrone sulfone compound 16-3, m.p. 170°–175°. IR(CHCl$_3$), $\nu$(cm$^{-1}$) 3020(w), 2940(m), 2020(w), 2020($\nu$s), 1970($\nu$s) (terminal metalcarbonyls), 1755(s), 1675(m). NMR(CDCl$_3$), δ(ppm) 7.4 and 6.8 (aromatic ring 3H); 5.5 and 4.9 (cyclopentadienyl protons, 4H); 2.8–0.6 complex resonances of the aliphatic steroid protons. The high resolution mass spectrum exhibited as parent peak the molecular ion with loss of the three metal carbonyls. Calculated for C$_{25}$H$_{27}$O$_5$MnS(M-3CO), 494.5; Found 494.0960.

EXAMPLE 17

Synthesis of Platinum-labelled Estriol Hapten

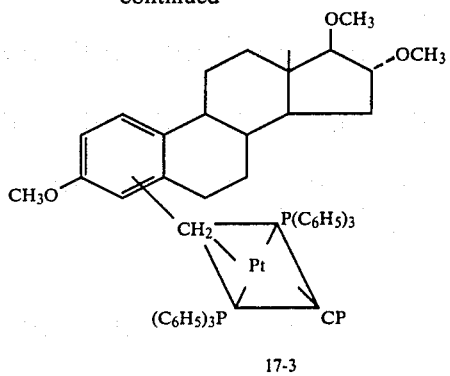

Step (i) - Synthesis of Chloromethyl-trimethoxyestriol

A solution of trimethoxy estriol, 17-1, (0.1 g, 0.29 m moles) and 3 drops of methyl chloromethyl ether in glacial acetic acid (1 ml) was stirred at room temperature for 17 hrs. The temperature was then raised to 60° C. and two 3-drop portions were added at 3 hr. intervals. The cooled reaction mixture was diluted with water (40 ml) and the white precipitate was collected by filtration, washed with water and dried in a dessicator over P$_2$O$_5$. Purification by preparative TLC (silica gel, 2% MeOH in CHCl$_3$) yielded a product (40 mg, 38% yield) which by NMR spectroscopy was shown to be a mixture of two isomers 2-chloromethyl- and 4-chloromethyl trimethoxy estriol, 17-2.

Step (ii) - Reaction of 17-2 with tetrakis (triphenyl phosphine) platinum

A solution of the chloromethylated mixture obtained in Step (i) above, (40 mg, 0.1 m moles) and [(C$_6$H$_5$)$_3$P [$_4$ Pt (85 mg, 0.68 m moles) in benzene (7 ml) was refluxed under nitrogen for 3 hrs. Work up by the same procedure as in Example 15 produced a compound which was purified by two successive preparative TLC plates (silica gel, 2% MeOH in CHCl$_3$) to yield 40 mg (67%) of the platinum compound 17-3, m.p. 135°–140° C. IR(CHCl$_3$), $\nu$(cm$^{-1}$), 1100(s), 1120(vs), 1170(vs), 1315(m), 1385(m), 1440(vs), 1490(m), 1600(s), several weak band between 1680–1990, 2880(s) and 2940(s).

NMR (CDCl$_3$) δ(ppm), 7.45 (broad multiplet (C$_6$H$_5$)$_3$P protons and aromatic steroid protons), 3.80 (broad singlet), 3.50 (singlet) and 3.35 (singlet) for the three methoxy CH$_3$ groups; 3.0–1.0 (steroid aliphatic protons); 0.90 (singlet) and 0.75 (singlet). The angular methyl groups of the two isomers, 17-3.

EXAMPLE 18

Synthesis of Gold-labelled Estradiol hemisuccinate Hapten

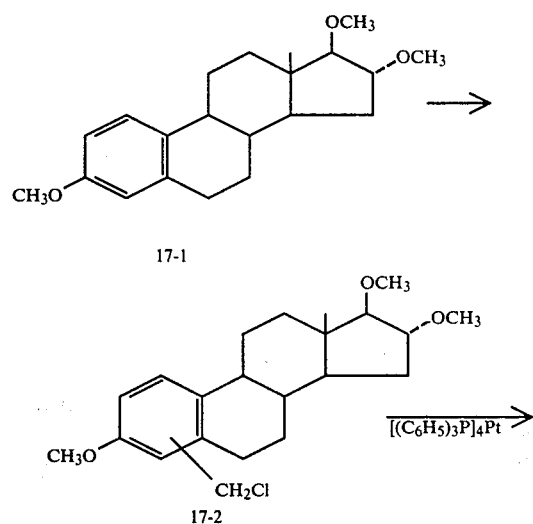

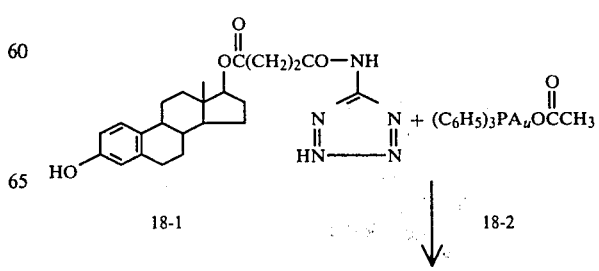

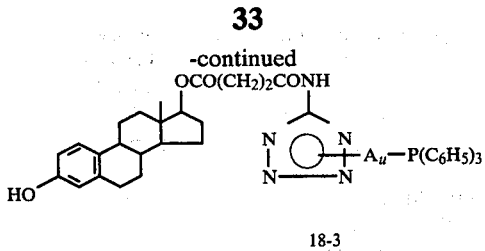

18-3

Step (i)

The active ester of estradiol hemisuccinate, prepared as in Example 6 Step (i) from E$_2$(HS)-COOH (0.186 g, 0.5 m moles), NHS (0.075 g, 0.65 m moles) and DCC (0.146 g, 0.71 m moles) was reacted with 5-aminotetrazole (0.1 g, 1.0 m mole) in DMF (5 ml). After stirring for 15 hrs. at room temperature, the solvent was evaporated in vacuum and the residue was extracted by a two phase, ethyl acetate-water (50 ml:10 ml), system. The ethyl acetate layer was separated, dried (MgSO$_4$), and evaporated off. The residue was recrystallized from methanol to aford a white crystalline material (0.06 g, 22% yield), m.p. ~ 195° C. The I.R. and NMR spectra showed this to be the tetrazole-substituted amide 18-1. IR(KBr),$\nu$(cm$^{-1}$): 1730(sh), 1710(s), 1630(s), 1580(m). NMR(CD$_3$OD), $\nu$(ppm) was virtually identical to that of the present compound E$_2$(HS)-COOH, except for the absence of the COOH resonance.

Step (ii)

A solution of triphenylphosphine gold acetate, 18-2 (0.06 g, 0.11m mole) in methanol (5 ml) was mixed with a solution of 18-1 (prepared in Step (i) above) (0.052 g, 0.12 m moles) in methanol (5 ml). The reaction mixture was stirred for 15 hrs. at room temperature and after removing the methanol solvent, the residue was extracted with THF (3×10 ml). The combined THF extracts were filtered and diethyl ether was added until a white solid precipitated. This was collected by filtration and recrystalized from THF/diethyl ether, affording the gold derivative 18-3 as white crystals (0.035 g, 35% yield). The NMR spectrum (DMSO-d$_6$) showed the triphenylphosphine resonance centered at $\delta$7.7; the aromatic protons of the steroid moiety at $\delta$7.0 and 6.55; the

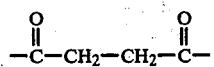

protons centered at $\delta$2.7; the angular methyl group at $\delta$0.68 and the broad resonance of the aliphatic protons of the steroid moiety between $\delta$3.0–0.9.

EXAMPLE 19

Synthesis of Manganese-labelled 1,3,5-Estratriene-3-ol-17-amino Haptens.

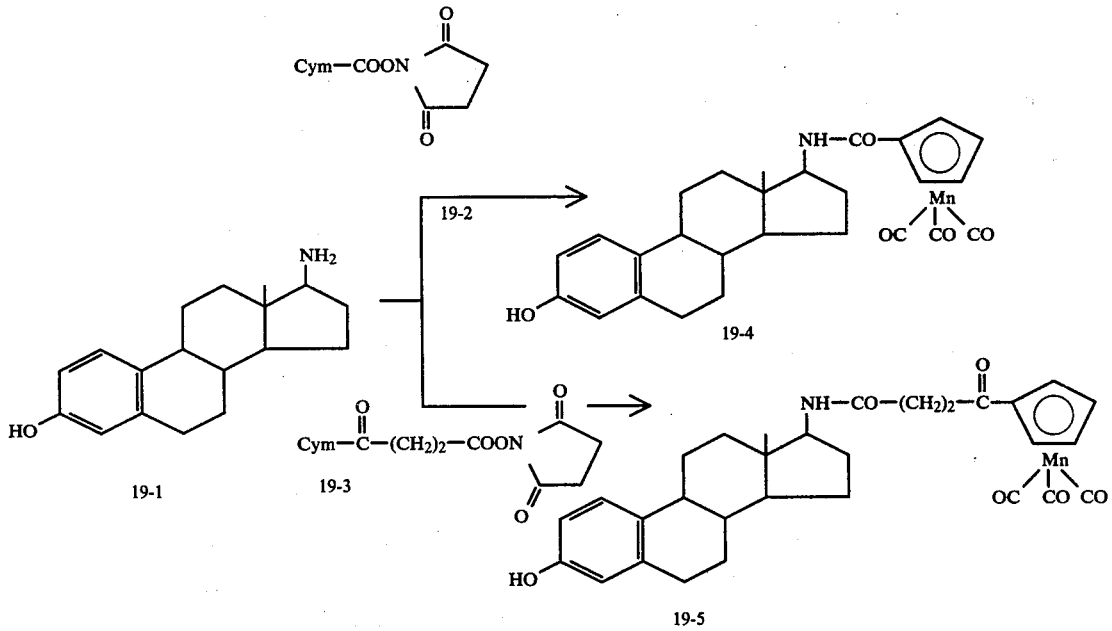

Cym = (CO)$_3$MnC$_5$H$_4$

Step (i) - Synthesis of cymantrenoyl-N-succinimide ester: 19-2

A solution of cymantrenylcarboxylic acid, Cym-COOH, (0.25 g) and N-hydroxysuccinimide (0.12 g) in THF was treated with DCC (0.23 g) at 0° C. for 2 hrs. under nitrogen. Stirring was continued at room temperature for 48 hrs., filtered to remove the precipitated urea and the solvent evaporated. The residue, which by IR and NMR was shown to be the active ester, 19-2, was used in the next step without further purification.

Step (ii) - Reaction of 19-2 with 1,3,5-Estratriene-3-ol-17-amino,E$_1$-NH$_2$.

The active ester obtained in Step (i) above was reacted with a solution of E$_1$-NH$_2$ (0.27 g, 1.0 m mole) in THF (10 ml), under nitrogen. After stirring at room temperature for 15 hrs., the solvent was evaporated in vacuum and the residue extracted by a two phase, ethyl acetate-water, system. The ethyl acetate layer was separated, dried (MgSO$_4$) and evaporated in vacuum. Purification by preparative TLC gave 0.26 g (53% yield) of the pure compound, m.p., 120°–121° which was shown by I.R., NMR and mass spectroscopy to be the cymantrenyl derivative, 19-4. The I.R. spectrum exhibited the typical metal carbonyl absorptions at 2050 and 1920 cm$^{-1}$ and the amide bands at 1680 and 1540 cm$^{-1}$. The NMR spectrum (CDCl$_3$) $\mu$(ppm) showed the estrogen aromatic protons at 7.16 and 6.60, the cyclopentadienyl ring protons at 5.33 and 4.75, the angular CH$_3$ group at 0.7 and the steroid aliphatic resonances between 3.0–0.9. The high resolution mass spectrum showed the molecular ion at m/e 501.1327 (calc. 501.4) and the parent peak (M-3CO) at m/e 417.1783.

Step (iii) - Synthesis of 4-oxo-4-cymantrenyl butanoate-N-succinimide ester, 19-3.

The active N-succimide ester 19-3 was prepared by the procedure described in Step (i) above from 4-oxo-4-cymantrenyl butanoic acid (0.29, 0.7 m mole), N-hydroxysuccinimide (0.08 g, 0.7 m mole) and DCC (0.18 g, 0.77 m mole) in THF.

Step (iv) - Reaction of 19-3 with 1,3,5-Estradiene-3-ol-17-amino,E$_1$-NH$_2$.

The active ester obtained in Step (iii) above was reacted with E$_1$-NH$_2$ by the same procedure as described in Step (ii) above. The final product, 19-5 obtained in 33% yield exhibited in the I.R. spectrum (CHCl$_3$9 the metal carbonyl bands at 2015 and 1950 cm$^{-1}$ and the amide bands at 1670 and 1500 cm$^{-1}$. The NMR spectrum (CDCl$_3$) δ(ppm): 7.2 and 6.6 (aromatic protons); 5.5 and 4.9 [cyclopentadienyl protons];

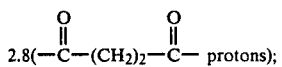

2.8(—C—(CH$_2$)$_2$—C— protons);

0.66 (angular CH$_3$); 2.5–0.9 (steroid aliphatic protons).

EXAMPLE 20

Synthesis of Cobalt-labelled 1,3,5-Estratriene-3-ol-17-amino Hapten.

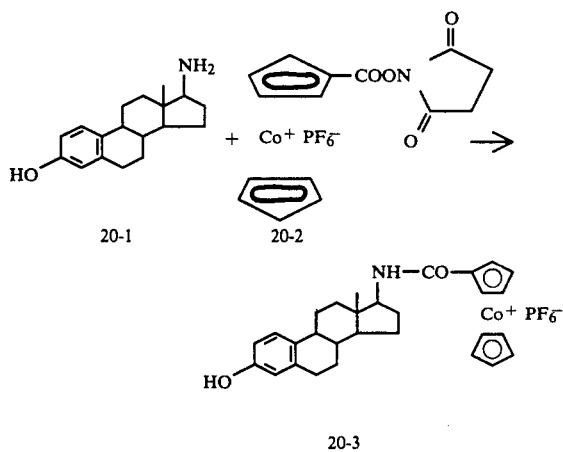

Step (i) - Synthesis of Cobalticenium Carboxylate N-succinimide ester, 20-2.

A solution of DCC (0.206 g. 1/0 m mole) in freshly distilled acetonitrile (10 ml) was added at 0° C. to a solution of cobalticenium carboxylic acid hexafluorophosphate (0.378 g, 1.0 m mole) and N-hydroxysuccinimide (0.115 g, 1.0 m mole) in acetonitrile (15 ml). After stirring at 0° C. for 2 hrs., the solution was allowed to come at room temperature and stirring was continued for 24 hrs. After filtration to remove the precipitated urea, the solvent was evaporated to yield 0.47 g of the active ester, 20-2. IR (KBr) ν(cm$^{-1}$): 3100, 2895, 2810, 1820, 1790(s), 1750(s), 1470, 1425, 1410, 1380, 1270(s), 1200(s), 1100(s), 1010, 900, 830(s). NMR(acetone-d$_6$) exhibited the unsubstituted cyclopentadienyl absorptions at δ6.2 (singlet) and the substituted cyclopentadienyl protons at 6.3δ (triplet) and 6.65δ (triplet).

Step (ii) - Reaction of 20-2 with E$_1$-NH$_2$

A solution of the active ester 20-2 (0.47 g) prepared in Step (i) above and E$_1$-NH$_2$ (0.273 g) in acetonitrile (15 ml) was stirred at room temperature for 24 hrs. After filtration, the solvent was evaporated in vacuum and the residue (0.693 g) was dissolved in minimum of acetone. The acetone solution was kept in the refrigerator for 2 hrs and filtered to remove precipitated impurities. The acetone filtrate was diluted with water and the yellow precipitate was collected by filtration, washed with several portions of water and dried to yield 0.46 g of the cobalticenium estrogen derivative, 20-3.

IR(KBr), (cm$^{-1}$) : 3250, 3100, 2920(s), 2850, 1775, 1700(s), 1625(s), 1500, 1420, 1390, 1270, 1250(s), 1220(s), 1160, 1100, 840(s).

NMR(acetone-d$_6$) (ppm) : 5.95 (singlet, unsubstituted C$_5$H$_5$ ring); 7.2–6.15 (steroid aromatic protons and the two triplets of the substituted cyclopentadienyl ring); 0.9 (angular CH$_3$), 2.8–1.0 (aliphatic steroid protons).

EXAMPLE 21

A Sephadex-column Immunoassay Procedure with a Cobalt-labelled Metallohapten.

One of the standard methods in common use for separation of the "bound" and "free" haptens in the antibody-antigen equilibrium system is by gel filtration with adsorbents of the sephadex type, a commercial product available from Pharmacia Fine Chemicals AB, Uppsala, Sweden. The following description of results illustrates how such a method could be employed with metallohapten reagents and can serve as a basis for undertaking the optimization of a metallo-immunoassay requiring the use of such a separation procedure.

Step (i) - Preparation of Columns and Reagents (A) Small columns of Sephadex G-10 were prepared in 3 ml plastic syringe barrels fitted at the bottom with porous ethylene discs. Sephadex G-10 was allowed to swell in water overnight. After the fines were removed by repeated suspension in de-ionized water, the supernatant water was removed as completely as possible and the sephadex gel was suspended three times in 0.01 M phosphate buffer, pH 7.5. The sephadex was allowed to settle for 2 hrs., the supernatant buffer was removed and an equal volume of fresh buffer was added to give a 50% suspension. While the suspension was being vigorously stirred, 2 ml of the slurry were pipetted into each syringe barrel. After the excess buffer had drained (1 ml) the syringe outlet was capped and the columns, containing 1 ml of Sephadex G-10 gel, were ready for use.

(B) A stock solution (93.35 μg Co/ml) of the cobalt-labelled estrogen hapten 20-3, synthesized as in Example 20, was prepared in 40% DMF - triply distilled water to which 0.2% (by volume) of supra pure nitric acid had been added. Dilute standards (in the range 0–0.4 μg Co/ml) were prepared in duplicates in 15% DMF/0.01 M phosphate buffer and each AA measurement was performed in duplicate to prepare the calibration curves.

(C) The anti-estradiol hemisuccinate antiserum used, R-27, Pool VII, had a concentration of 4.2×10$^{-5}$M antibody sites. For controls, normal rabbit serum, R-49 was used in these experiments.

Step (ii) - Assay procedure

Four columns, prepared in duplicate as described in Step (i) (A), were numbered 1 to 4, with the suffix a or b to denote duplicates of the same columns, e.g., 1a, 1b; 2a, 2b, etc. Columns 1,3 and 4 were the controls, column 2 was the assay column. The stock solution from Step (i) (B) was diluted to obtain a working solution of the metallohapten (2.43 μg Co/ml). The sequential addition of reagents, summarized in Table 21-1, was the following:

Table 21-1

| Sequence of Reagents Addition | | Column No. 1 | | 2 | | 3 | | 4 | |
|---|---|---|---|---|---|---|---|---|---|
| | | a | b | a | b | a | b | a | b |
| (1) | Metallohapten solution (ml) | 0.24 | 0.24 | 0.24 | 0.24 | — | — | — | — |
| | Buffer solution (ml) | — | — | — | — | 0.24 | 0.24 | 0.24 | 0.24 |
| (2) | Buffer solution (ml) | 1.0 | 1.0 | 1.0 | 1.0 | 1.0 | 1.0 | 1.0 | 1.0 |
| (3) | Antiserum solution (ml) | — | — | 0.2 | 0.2 | — | — | 0.2 | 0.2 |
| | Buffer solution (ml) | 0.2 | 0.2 | — | — | 0.2 | 0.2 | — | — |
| (4) | Buffer solution (ml) | 2.0 | 2.0 | 2.0 | 2.0 | 2.0 | 2.0 | 2.0 | 2.0 |

(1) A constant volume (0.24 ml) of the metallohapten working solution was added to columns 1 and 2 (0.24 ml, equivalent to an absolute value of 0.58 μg Co) and the same volume (0.24 ml) of the buffer solution was added to columns 3 and 4. The columns were allowed to drain and the effluent from each column, collected in polyethylene test tubes, showed no cobalt present when assayed for Co by AA.

(2) In the next step, the syringe outlet of the columns was capped, 1 ml of buffer was added to each column and after mixing the gel with a Vortex mixer, the columns were allowed to drain, the effluents being collected as previously and assayed for Co by AA. The effluents from columns 1 through 2 gave an average of 0.12 μg Co and none in the effluents from columns 3 through 4.

(3) To each column was then added a volume of 0.2 ml, antiserum to columns 2 and 4 or buffer solution to columns 1 to 3. The drained effluent from all columns, 1 through 4 showed no cobalt by AA.

(4) The columns were allowed to incubate at room temperature for 90 min. and two 1 ml portions of buffer were added to each column and the drained effluents collected separately. When assayed for Co by AA, the effluents from columns showed the non-specific removal of an additional 0.13 μg Co out of the 0.46 μg Co left on the column after Step (2) above. However, the effluent from the assay column 2, to which antiserum had been added, showed a content of 0.43 μg Co, equivalent to a 94% recovery of the metallohapten originally applied to the column. The effluents from columns 3 and 4, as expected showed no Co present.

In an additional control experiment, where the antibody solution added to column 2 was replaced by normal rabbit serum γ-globulins the non-specific elution of metallohapten in both columns 1 and 2 was between 0.18 and 0.25 μg Co.

The Sephadex column procedure described above was adapted to one reported in the literature [Clin.-Chem., 21, 1805 (1975)] for an estriol radioimmunoassay. It sould be clearly understood that the conditions reported in Example 21 could be optimized by anyone skilled in the art, to reduce the amount of non-specific elution of hapten, fitting appropriate assay procedure parameters for each individual hapten to be assayed.

EXAMPLE 22

An Ammonium Sulfate Precipitation Immunoassay Procedure with a Cobalt-labelled Metallohapten A relatively simple and inexpensive procedure for separation of the "bound" and "free" haptens in the antibody-hapten equilibrium system is protein precipitation by addition of a concentrated solution of a salt such as ammonium or sodium sulfate. This precipitates the "bound" component leaving the "free" in solution and the amount of labelled hapten can be determined by using either the precipitate or the supernatant. The following description of results illustrates a non-optimized example of the application of such a method using metallohapten reagents. Optimization conditions can be easily developed for each individual hapten.

Step (i) - Preparation of Reagents

A stock solution of the cobalt-labelled estrogen, 20-3 was prepared as in Example 20, Step (i)(B) with a concentration of 93.35 μg Co/ml. The working solution (1.86 μg Co/ml) for calibration standards was acid (65%) and completed to 5 ml volume with 0.01 M phosphate buffer. The working solution (0.187 μg Co/ml) for the antibody-hapten reactions was prepared by taking 50 μl of the stock solution, 3.73 ml DMF, 50 μl suprapane nitric acid (65%) and completion to 25 ml with 0.01 M phosphate buffer.

The anti-estradiol hemisuccinate antiserum used, R-27, Pool VIII, had a concentration of $7.84 \times 10^{-5}$ M antibody sites. For controls, NRS, normal rabbit serum, R-49, was used.

The precipitating solution was made from ammonium sulfate (7.6 g), water (12 ml) and DMF (1.5 ml).

Step (ii) - Procedure to determine assay conditions

1. Twenty semi-micro polyethylene tubes were numbered 1a,1b, 2a,2b up to 10a,10b to provide duplicates of each preparation.
2. A fixed volume (100 μl) of the metallohapten working solution (0.187 μg Co/ml) was pipetted into each tube from 1 through 9. In tubes 10, 100 μl of phosphate buffer were pipetted in place of the metallohapten.
3. Portions of 10,20,30 and 50 μl of NRS were added to tubes 1,2,3 and 4 respectively to serve controls for non-specific adsorption.
4. Portions of 10,20,30,40 and 50 μl of antiserum were added to tubes 5,6,7,8, and 9 respectively, as well as 50 μl of antiserum to tube 10.
5. All the tubes were Vortex-mixed and allowed to incubate at room temperature for 45 min.
6. A constant volume (200 μl) of ammonium sulfate solution was added to each tube and Vortex-mixed.
7. After centrifugation at room temperature for 20 min. at 2000 G, the supernatant was discarded, the test-tubes were inverted on tissue paper and allowed to drain for 5 minutes.

8. A constant volume (100 μl) of a phosphate buffer solution was added to each tube and after Vortex mixing, aliquots (30 μl) were drawn with an Eppendorf pipette and injected into the graphite chamber of the atomic absorption instrument. The results showed that the precipitates from tubes 1 through 4 (NRS controls) as well as tube 5 (10 μl antiserum) and tube 10 (no hapten added) contained 6% or less of "bound" cobalt-labelled hapten. Tubes 6,7,8 and 9 contained 50%, 68%, 76% and 85% respectively of "bound" cobalt-labelled hapten.

A similar experiment was carried out using a fixed volume of antiserum (30 μl) and adding varying volumes (20-100 μl) of metallohapten, making up the difference to a constant total volume (130 μl) with phosphate buffer. These two sets of experiments afford the choice of appropriate mixtures of antisera and metallohapten dilutions for a competitive binding assay.

EXAMPLE 23

Synthesis of a Palladium Reagent and a Palladium-labelled Estrogen Hapten

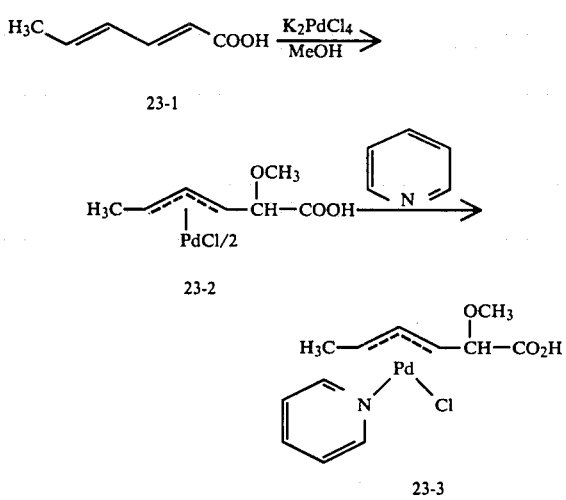

Step (i) - Synthesis of a pi-allylpalladium sorbic acid complex dimer, 23-2

To a stirred suspension of potassium tetrachloropalladite, $K_2PdCl_4$ (2.09, 6.12 m moles) in water (30 ml) was added sorbic acid, 23-1 (1.5 g, 12.3 m moles) followed by methanol (250 ml) and water (20 ml). Stirring was continued for 1 hr. until all the solid particles went in solution. The reaction mixture was concentrated to about one third the volume in vacuum on a rotary evaporator and the yellow precipitate collected by filtration washed with several portions of water and dried in vacuum to yield 1.1 g (38% yield) of yellow crystals, m.p. 170°-173° C. The IR (KBr) showed the carbonyl band at 1690 cm$^{-1}$ and the NMR spectrum (in deuteropyridine) showed resonances in support of structure 23-2, or its isomer where the $OCH_3$ group is situated on the alpha position to the terminal methyl group; δ(ppm), 1.42 (doublet, $CH_3$), 3.46 (singlet, $OCH_3$), 3.72-4.65 (multiplet, terminal allyl protons), 6.72 (triplet, central allyl proton).

Step (ii) - Synthesis of a pi-allylpalladium sorbic acid complex monomer, 23-2

The dimer pi-allylpalladium derivative, 23-2, obtained in Step (i) above (0.2 g, 0.435 m mole) was suspended in methylene chloride (5 ml) and pyridine (0.2 ml, 2.6 m mole) was added dropwise under reflux. All the solid went in solution upon addition of the pyridine and the yellow solution was evaporated in vacuum. The solid residue was washed several times with light petroleum ether to remove unreacted pyridine and dried in vacuum to yield 0.13 g (50% yield) of yellow solid, m.p. 65°-70° C., soluble in organic solvents such as chloroform and methylene chloride. The IR (CHCl$_3$) showed the carbonyl band at 1720 cm$^{-1}$ and the NMR spectrum (CDCl$_3$) exhibited the expected resonances for structure 23-3: δ(ppm): 7.55 (multiplet, pyridine protons): 6.4 (triplet, central allyl proton); 3.7-4.1 (multiplet, terminal allyl protons); 3.45 (singlet, $OCH_3$); 1.4 (doublet, terminal $CH_3$).

Similar monomers can be prepared by the use of other ligands, such as β-diketonates and cyclopentadienyls, which are known to displace the chlorobridges in pi-allyl palladium chloride dimers.

Step (iii) - Synthesis of N-succinimide active ester, 23-4

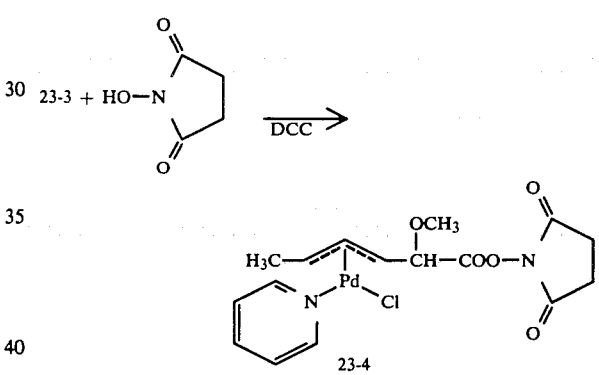

A solution of DCC (40 mg) in THF (2 ml) was added under stirring to a cooled solution (0°) of the palladium complex, 23-3 (60 mg, 0.19 m moles) and N-hydroxysuccinimide (22 mg, 0.19 m mole) in THF (5 ml). Stirring at 0° C. was continued for 2 hr. and then for an additional 2 hr. at room temperaure. The white precipitate formed in the reaction was removed by filtration and the yellow filtrate was evaporated in vacuum. The residue was extracted with methylene chloride and the yellow coloured organic extract was evaporated in vacuum to yield a yellow solid which was shown by IR (KBr) to be the succinimide ester, 23-4. ($ν_{CO}$ 1820, 1780 and 1745 cm$^{-1}$). This compound can serve as a general reagent for labelling haptens with palladium by reacting it with an aminofunctional group present in the hapten, as for example 1,3,5-estratirene-3-ol-17-amino, E$_1$-NH$_2$, or amphetamine (1-phenyl-2-aminopropane).

EXAMPLE 24

Synthesis of Cobalt-labelled Bovine Serum Albumin and its reaction with Anti-BSA Antibodies Step (i) - Cobalt-labelling of BSA A solution of carboxycobalticenium N-succinimide ester, (0.15 g, 0.236 m mole), prepared as in Example 20, Step (i), in acetonitrile (2 ml) was added to a cooled solution of BSA (0.15 g, 2.36×10$^{-6}$ mole) in water (20 ml). After addition of several drops of triethylamine to adjust the alkalinity to pH 10, the reaction mixture was stirred at 4° C. for 48 hrs. The solution was then dialyzed against a water/acetonitrile system (twice) and then against distilled water (three times). Lyophilization of the dialysate yielded 117 mg of a yellowish fluffy powder, shown to be the BSA-(carboxycobalticenium) conjugate.

Step (ii) - Determination of n (number of metallohapten labelling molecules) in BSA-conjugate (A) The following stock solutions were prepared:
(1) BSA stock solution ($10^{-6}$M):3.2 mg BSA dissolved in 50 ml water.
(2) Carboxycobalticenium stock solution ($10^{-3}$M): 3.2 mg carboxycobalticenium $PF_6$ salt in 10 ml of 40% $DMF/H_2O$ solution.
(3) BSA - cobalt labelled conjugate stock solution: 4.2 mg of BSA conjugate obtained in Step (i) above, dissolved in 50 ml of 16% $DMF/H_2O$ solution.

(B) Two calibration curves were determined by atomic absorption measurements:

Calibration (1) a series of dilutions of carboxycobalticenium salt in 15% $DMF/H_2O$ (to a total volume of 300 ml) in the range between 0 and 0.39 µg Co/ml. The linear regression equation $Y=71.654x+3.296$ had a correlation coefficient $r=0.9933$ Calibration (2): The same series of dilutions of carboxycobalticenium salt as in calibration curve (1) with the addition of a constant volume (60 µl) of the BSA stock solution to a total volume of 300 µl. The linear regression equation $Y=62.034x +2.2$ had a correlation coefficient $r=0.9995$.

(3) The BSA-cobalt labelled conjugate stock solution was diluted 1:10 and 1:20 and measured by atomic absorption under the same instrument conditions as in for calibration curve (2). The height of the signals 22 mm and 12 mm respectively was interpolated for Y in the linear equation giving a concentration of 0.275 µg Co/ml and 0.136 µg Co/ml for the two dilutions, corresponding to a concentration of 2.735 µg Co/ml in the original BSA conjugate stock solution, equivalent to $46.4 \times 10^{-9}$ Co atom/ml. Since the stock solution containing 4.2 mg of BSA - conjugate in 50 ml was equivalent to $1.3 \times 10^{-9}$ BSA mole/ml, the number of cobalticenium haptens per mole of BSA in the labelled conjugate was $n = 46.4 \times 10^{-9}/1.3 \times 10^{-9} \approx 35$ Step (iii) - Interaction of Cobalt-labelled BSA conjugate with anti-BSA antibodies A simple procedure to determine the antibody-antigen interaction quantitatively by atomic absorption as shown in the following example.

Two sets of duplicated tubes were prepared as follows:

(1) Anti-BSA antiserum (100 µl) was added to each of four tubes numbered 1 to 4. The same volume (100 µl) of 0.01 M phosphate buffer was added to each of additional four tubes, numbered 5 to 8.
(2) A fixed volume (100 µl) of four dilutions of BSA-Cobalt labelled conjugate, containing 0.23, 0.47, 0.94 and 1.88 µg Co/ml (or 0.8, 1.6, 3.1 and 6.2 µg BSA conjugate/100 µl of sample) added to the tubes 1 to 4 respectively and similarly to tubes 5 to 8 respectively.
(3) The solutions were mixed on a Vortex, allowed to incubate for 1 hr. at 37° C. and then for 48 hrs. at 4° C.
(4) The tubes were then centrifuged for 30 min. at 4° C.
(5) The supernatant was analyzed for Co by atomic absorption.

The readings obtained from tubes 5 through 8 served as calibrating controls. The readings from tubes 1 through 4 then indicated the amount of free cobalt-labelled BSA left in solution (by difference the "bound" BSA antigen could be determined). The atomic absorption measurements were interpolated into the calibration curve and gave 0.00, 0.06, 0.59 and 1.25 µg Co/ml of "free" hapten, equivalent to a concentration of 0,0.2,2.0 and 4.3 µg BSA conjugate/100 µl of original sample in tubes 1,2,3 and 4 respectively.

Variations of the above procedure can be devised to suit the problem in hand. For example, it is possible to label the antibody-proteins with one type of metallohapten and the antigen protein with a different-metal-label and then determine by atomic absorption each metal separately. The precipitated antibody-antigen complex could be collected and resuspended in a suitable solvent for atomic absorption measurement of the two different metals. It is also possible to label the same hapten with two or more different metals. For example we have reacted BSA with a mixture of N-succinimide active esters of the carboxycobalticenium and carboxycymantrene, or of carboxyferrocene and carboxycymantrene to obtain mixed cobalt and manganese - or mixed iron and manganese-labelled BSA hapten.

I claim:

1. A heterogeneous specific binding assay method for assaying a liquid medium for a ligand, which method comprises:

(a) contacting said liquid medium with reagent means which includes a metal (metallo-hapten, metallo-binder) labelled constituent comprising a conjugate of a metal labelling substance and a binding component and which forms, with said ligand to be determined, a binding reaction system producing a metal-containing bound-phase and a metal-containing free-phase of said metal labelled constituent, the quantity of metal labelling substance resulting in said metal-containing bound-phase and metal-containing free-phase being a function of the amount of said ligand present in said liquid medium.

(b) separating said metal-containing bound-phase from said metal-containing free-phase; and (c) measuring the metal content in either said bound-phase or said free-phase.

2. A method as in claim 1 wherein said labelled constituent comprises a conjugate of said ligand or a specific binding analog thereof and at least one metal atom.

3. A method as in claim 2, wherein said labelled constituent comprises said ligand or a specific binding analog thereof into which said at least one metal atom has been introduced.

4. A method as in claim 2 wherein said labelled constituent comprises said ligand or a specific binding analog thereof bound to a metal organo-derivative.

5. A method as in claim 4, wherein said metal organo-derivative is represented by the general formula

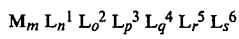

wherein M is said at least one metal atom, $L^1$ through $L^6$ are ligands or specific binding analogs thereof, which may be the same or different, m is an integer between 1 and 10, and n,o,p,q,r and s are integers between 0 and 12 provided that their sum does not exceed the coordination number of $M_m$.

6. A method as in claim 4, wherein said metal organo-derivative is an organo-metallic compound or a metal coordination complex.

7. A method as in claim 6, wherein said organo-metallic compound is characterized by covalent bonding.

8. A method as in claim 5, wherein said organo-metallic compound is characterized by pi-bonding.

9. A method as in claim 1, wherein the amount of said metal content in either said separated bound-phase or free-phase is determined by atomic absorption or emission spectrophotometry.

10. A method as in claim 1, wherein the metal is selected from the transition metals of group I B, II B, III B, IV B, V B, VI B, VII B and VIII of the Periodic Table of elements.

11. A method as in claim 1, wherein said reagent comprises a specific binding partner of said ligand and a metal-labelled conjugate bound thereto, said conjugate comprising said metal atom and said ligand or a specific binding analog thereof.

12. A method as in claim 10, wherein said specific binding partner is in an insoluble form.

13. A method as in claim 1, wherein said ligand is selected from the group consisting of antigens, haptens, and antibodies thereto; hormones, vitamins, drugs, metabolites and their receptors and binding substances.

14. A method as in claim 1, wherein said ligand is a drug or a metabolite thereof.

15. A method as in claim 14, wherein said drug is a hormone or an antagonist thereof.

16. A method as in claim 15, wherein said hormone is a steroid.

17. A method according to claim 1, wherein said ligand is selected from the group consisting of antibiotic, tranquilizer, vitamin, narcotic, cannabinoid, barbiturate or alkaloid.

18. Reagent means for use in assaying a liquid medium for a ligand, which reagent means includes a metal labelled constituent comprising a conjugate of a metal labelling substance and a binding component and which forms, in combination with said ligand, a specific binding reaction system producing a metal-containing bound-phase and a metal-containing free-phase of said labelled constituent, the quantity of labelling metal resulting in said metal-containing bound-phase being a function of the amount of said ligand present in said liquid medium, characterized in that said labelling substance is at least one metal atom which can be exactly measured.

19. Reagent means for use in assaying a liquid medium for a ligand as in claim 18, wherein the metal content is determined by atomic absorption or emission spectrophotometry.

20. Reagent means as in claim 18, wherein said metal labelled constituent comprises a conjugate of said ligand or a specific binding analog thereof and at least one metal atom.

21. Reagent means as in claim 20, wherein said metal labelled constituent comprises said ligand or a specific binding analog thereof into which said at least one metal atom has been introduced.

22. Reagent means as in claim 20, wherein said metal labelled constituent comprises said ligand or a specific binding analog thereof bound to a metal organo-derivative.

23. Reagent means as in claim 22, wherein said metal organo-derivative is represented by the general formula

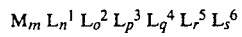

wherein M is said metal atom, $L^1$ through $L^6$ are ligands or specific binding analogs thereof, which may be the same or different, m is an integer between 1 and 10, and n,o,p,q,r and s are integers between 0 and 12 provided that their sum does not exceed the coordination number of $M_m$.

24. Reagent means as in claim 22, wherein said metal organo-derivative is an organo-metallic compound or a metal coordination complex.

25. Reagent means as in claim 24, wherein said organo-metallic compound is characterized by covalent bonding.

26. Reagent means as in claim 24, wherein said organo-metallic compound is characterized by pi-bonding.

27. Reagent means as in claim 18, which comprises (i) a conjugate of said at least one metal atom and said ligand or a specific binding analog thereof and (ii) a specific binding partner of said ligand.

28. Reagent means as in claim 27, wherein said conjugate and said binding partner are bound together through said ligand or analog thereof.

29. Reagent means as in claim 28, wherein said binding partner is in an insoluble form.

30. Reagent means as in claim 27, wherein said binding partner is in an insoluble form and said conjugate is in a soluble form.

31. Reagent means as in claim 27, wherein said conjugate is in an insoluble form and said binding partner is in a soluble form.

32. Reagent means as in claim 18, which comprises (i) a soluble conjugate of said at least one metal atom and a specific binding partner of said ligand and (ii) an insoluble form of said ligand or a specific binding analog thereof.

33. Reagent means as in claim 18, which comprises (i) a soluble conjugate of said at least one metal atom and a specific binding partner of said ligand and (ii) an insoluble form of a specific binding partner of said ligand.

34. Reagent means as in claim 18, wherein the metal is a metal or combination of metal elements, selected from the transition metals of group I B, II B, III B, IV B, V B, VI B, VII B and VIII of the Periodic Table of elements.

35. Reagent means as in claim 34 wherein the metal is a metal or combination of metal elements selected from Fe, Hg, Cr, Co, Pd, Pt, Au, Mn, Cu.

* * * * *